(12) United States Patent
Sankai

(10) Patent No.: US 8,574,176 B2
(45) Date of Patent: Nov. 5, 2013

(54) REHABILITATION SUPPORTING DEVICE

(75) Inventor: Yoshiyuki Sankai, Tsukuba (JP)

(73) Assignee: University of Tsukuba, Ibaraki (JP)

(*) Notice: Subject to any disclaimer, the term of this patent is extended or adjusted under 35 U.S.C. 154(b) by 568 days.

(21) Appl. No.: 12/531,730

(22) PCT Filed: Mar. 17, 2008

(86) PCT No.: PCT/JP2008/054890
§ 371 (c)(1),
(2), (4) Date: Sep. 17, 2009

(87) PCT Pub. No.: WO2008/123040
PCT Pub. Date: Oct. 16, 2008

(65) Prior Publication Data
US 2010/0130893 A1    May 27, 2010

(30) Foreign Application Priority Data

Mar. 22, 2007 (JP) .................... 2007-075632
Mar. 6, 2008 (JP) .................... 2008-056674

(51) Int. Cl.
*A61H 1/00* (2006.01)
(52) U.S. Cl.
USPC .............................. 601/5; 601/33
(58) Field of Classification Search
USPC ............ 601/5, 23, 33, 34, 35, 84; 600/587; 623/25
See application file for complete search history.

(56) References Cited

U.S. PATENT DOCUMENTS

| | | | |
|---|---|---|---|
| 6,872,187 | B1 | 3/2005 | Stark et al. |
| 2005/0101887 | A1* | 5/2005 | Stark et al. ................... 601/5 |
| 2005/0107726 | A1 | 5/2005 | Oyen et al. |
| 2006/0277074 | A1 | 12/2006 | Einav et al. |
| 2006/0293617 | A1 | 12/2006 | Einav et al. |
| 2007/0155588 | A1 | 7/2007 | Stark et al. |
| 2008/0071386 | A1* | 3/2008 | McBean et al. ............. 601/34 |

FOREIGN PATENT DOCUMENTS

| | | |
|---|---|---|
| JP | 07-163607 | 6/1995 |
| JP | 10-258100 | 9/1998 |
| JP | 2002-523182 | 7/2002 |
| JP | 2003-199799 | 7/2003 |

(Continued)

OTHER PUBLICATIONS

English translation for JP 2005-253650.*
Russian Office Action dated Nov. 1, 2010 with English translation.

*Primary Examiner* — Quang D Thanh
(74) *Attorney, Agent, or Firm* — IPUSA, PLLC

(57) ABSTRACT

A rehabilitation supporting device 1 includes a first frame 11 arranged along a first skeletal portion extending from a joint, a second frame 12 arranged along a second skeletal portion extending from the joint in a direction different from a direction of the first skeletal portion, an angle sensor 131 arranged to detect a rotational angle position between the first frame and the second frame, a flexion-side biosignal sensor 14 arranged to detect a biosignal of a flexor, an extension-side biosignal sensor 15 arranged to detect a biosignal of an extensor, a calibration unit 31 arranged to determine a flexion-side correction value and an extension-side correction value individually, and a memory unit 34 arranged to store individual correction values of the biosignals different for individuals, the flexion-side correction value, and the extension-side correction value.

11 Claims, 15 Drawing Sheets

(56) References Cited

FOREIGN PATENT DOCUMENTS

| JP | 2005253650 | 9/2005 |
| JP | 2005-278706 | 10/2005 |
| JP | 2006-204426 | 8/2006 |
| WO | WO03046287 | 6/2003 |
| WO | WO 2005/074371 | 8/2005 |
| WO | WO 2005/087172 | 9/2005 |
| WO | WO2006080134 | 8/2006 |

* cited by examiner

REHABILITATION SUPPORTING DEVICE

TECHNICAL FIELD

This invention relates to a rehabilitation supporting device which detects a biosignal from a body surface of a living body with a physical disability when the living body is in action, and supports rehabilitation for recovery of a physical ability of the living body.

BACKGROUND ART

In the existing institutions, such as medical institutions and sanatoriums, rehabilitation for recovery of a physically impaired person is performed by an exercise therapy to retrieve a physical ability of a moving part (such as a hand, an arm, a shoulder, a waist, a knee, an ankle, etc.) of the person (human body).

The medical rehabilitation of this type is performed by adding load to or applying external force to the muscles around the moving part to bend or stretch a joint of the moving part, in order to recover the physical ability of the moving part which decrease to direct or indirect factors, such as an injury or illness.

There are various methods of applying a load or an external force, such as a simple method using a weight or an elastic band and a machine-implemented method using a dedicated load machine or instrument. In any case, rehabilitation is carried out according to instructions of a doctor or a physiotherapist.

Patent Document 1 discloses a rehabilitation device which performs rehabilitation (or ergotherapy) by an exercise cure. The rehabilitation device includes an arm extending from the base part and a holding part disposed at a leading end of the arm. Using the rehabilitation device, the person who is subjected to rehabilitation can perform selectively one of several exercises in accordance with the recovering situation of the joint or muscular force of the person, the exercises including a compulsory exercise in which the limb of the person is compulsorily moved by an external force, an automatic exercise in which the limb of the person is actively moved, such as an isotonic motion, a uniform motion, and a resistance exercise.

The arm is the multi-axial link including two or more drive shafts. The arm moves the holding part to an arbitrary position in a movable range and changes the posture of the holding part. The arm moves along with the rail. The holding part is attached to the limb of the person who is subjected to rehabilitation. An angle sensor and a speed sensor are disposed on each of the drive shafts.

As disclosed in Patent Document 1, the rehabilitation device is arranged to acquire load information including the information of myoelectric signals produced by main muscles of the limb, the information of the position and posture of the arm, the detection value of a torque sensor attached to the drive shaft, etc., in order to measure the load which is actively produced by the limb of the person subjected to rehabilitation.

The acquired load information is used to perform an automatic assist. When the person moves the limb with his intention at the time of the automatic assist, a force larger than the force of the person is exerted on the limb by the auxiliary operation of the arm performed by the rehabilitation device based on the load information acquired at this time.

Patent Document 2 discloses a portable electromyogram and physical movement measuring device which is adapted for quantitatively analyzing the degree of recovery of the person by rehabilitation. This measuring device includes a myoelectric sensor and a physical movement sensor. The myoelectric sensor detects a myoelectric potential signal as a biosignal. In Patent Document 2, an acceleration sensor is used as the physical movement sensor. These sensors are disposed at symmetrical positions on each of the right-hand side and the left-hand side of the limbs of the person respectively, and the sensors disposed on one side cover the measuring part of the person while the sensors disposed on the other side cover the healthy part of the person.

The measuring device of Patent Document 2 transmits the detection signals output from the respective sensors, to an external personal computer through a radio transmission unit of the measuring device. The measurement data of the moving condition of the person acquired from the sensors is converted into numerical data, and displayed on the computer display. Viewing the numerical data on the display, a doctor or a physiotherapist analyzes quantitatively the effect of the rehabilitation to the person.

Patent Document 3 discloses a motor-driven auxiliary device which is attached to a knee joint of a person and assists the person who walks up a staircase. The motor-driven auxiliary device includes an actuator, an angle sensor, a pressure sensor, and a myoelectric sensor that detects a myoelectric potential as a biosignal. The angle sensor detects a rotational angle of the knee joint. The myoelectric sensor detects the degree of strain of the muscles. The pressure sensor detects a load or a weight on the leg. The motor-driven auxiliary device determines whether the motion of the person is a staircase walking operation based on the detection signals from these sensors and controls the driving of the actuator by using the detection signals of these sensors as a trigger.

Patent Document 1: Japanese Laid-Open Patent Publication No. 10-258100
Patent Document 2: Japanese Laid-Open Patent Publication No. 2005-278706
Patent Document 3: Japanese Laid-Open Patent Publication No. 7-163607

DISCLOSURE OF THE INVENTION

Problem to be Solved by the Invention

If a muscular force or a movable range of a moving part of a person declines from the state when the person was healthy, medical rehabilitation adequately fulfills the job of recovering the muscular force or the movable range of the moving part to the original state. For example, stretching of the muscles is performed or exercises of repeated moving operation are performed in order to strengthen the muscles.

However, if a person has a physical disability (for example, the person loses a physical ability or a moving part of the person is paralyzed) due to impairment of the brain or the spinal column, much time and patience is needed for recovery of the person, and it is uncertain whether the person will recover the lost physical ability by rehabilitation. Therefore, in many cases, the person gives up recovering or performs auxiliary training so that an operation of the disabled part is performed by other bodily parts.

In such circumstances, if a long time elapses after the physical disability arises, the muscular force and the movable range may decline significantly and the person may forget operation and feeling when healthy. In particular, in a daily operation which is performed by moving the muscles unconsciously, the person who loses the physical ability may forget the way the muscles are moved.

An exercise program of rehabilitation is carefully determined by repeatedly performing a dialog between an instructor (such as, a doctor or a physiotherapist) and a person who is subjected to rehabilitation and by checking whether the exercise program is appropriate for the person. Therefore, the exercise program varies in its content depending on the individual difference for each person as well as on the grade of the impairment or the degree of the recovery.

When the content of the exercise program is determined, the instructor of rehabilitation sometimes applies a load directly to the arm or the leg of the person to look into a reaction of the moving part of the person or ask the person about a feeling of the moving part. However, the person usually moves the muscles of the moving part unconsciously and there is an individual difference in the feeling for every person. It is difficult for the person to express the feeling quantitatively. If the communication between the instructor and the person does not go well, a suitable instruction of rehabilitation cannot be offered, which may prevent the recovery of the physical ability.

In an aspect of the invention, the present disclosure provides a rehabilitation supporting device which is able to take a correlation between a physical quantity around a joint as an object of measurement and a biosignal of a voluntary muscle around the joint, and output the correlation between the physical quantity and the biosignal in a quantitative manner.

Means for Solving the Problem

In an embodiment of the invention which solves or reduces one or more of the above-mentioned problems, the present disclosure provides a rehabilitation supporting device including: a first frame arranged along a first skeletal portion extending from a joint as an object of measurement among moving parts of a living body; a second frame arranged along a second skeletal portion extending from the joint in a direction different from a direction of the first skeletal portion; an angle sensor a center of rotation of which is arranged to be coaxial with a rotation axis of the joint, the angle sensor detecting a rotational angle position between the first frame and the second frame; a flexion-side biosignal sensor arranged to contact a body surface corresponding to a flexor which bends the first skeletal portion and the second skeletal portion bent around the joint, the flexion-side biosignal sensor detecting a biosignal of the flexor; an extension-side biosignal sensor arranged to contact a body surface corresponding to an extensor which stretches the first skeletal portion and the second skeletal portion around the joint, the extension-side biosignal sensor detecting a biosignal of the extensor; a calibration unit arranged to determine a flexion-side correction value to correct an output value of the flexion-side biosignal sensor and an extension-side correction value to correct an output value of the extension-side biosignal sensor individually; and a memory unit arranged to store individual correction values of the biosignals different for individuals, the flexion-side correction value, and the extension-side correction value.

In an embodiment of the invention which solves or reduces one or more of the above-mentioned problems, the present disclosure provides the rehabilitation supporting device wherein the flexion-side biosignal sensor measures, as the biosignal of the flexor, at least one of a flexion-side neurotransmission signal corresponding to the flexor, sent from a brain to contract the flexor, and a flexion-side myoelectric potential signal arising when the flexor is contracted, and the extension-side biosignal sensor measures, as the biosignal of the extensor, at least one of an extension-side neurotransmission signal corresponding to the extensor, output from the brain to contract the extensor, and an extension-side myoelectric potential signal arising when the extensor is contracted.

In an embodiment of the invention which solves or reduces one or more of the above-mentioned problems, the present disclosure provides the rehabilitation supporting device further including an indicating unit arranged to provide visual, audio or tangible information which is recognized by at least one of vision, hearing and tactile senses, and the indicating unit is arranged to output the information based on a flexor output signal obtained from an output value of the flexion-side biosignal sensor which is corrected based on the flexion-side correction value, an extensor output signal obtained from an output value of the extension-side biosignal sensor which is corrected based on the extension-side correction value, and the rotational angle position detected by the angle sensor.

In an embodiment of the invention which solves or reduces one or more of the above-mentioned problems, the present disclosure provides the rehabilitation supporting device wherein the calibration unit is arranged to determine the flexion-side correction value and the extension-side correction value based on an amount of change of a rotational angle detected by the angle sensor, a time for the first frame being rotated to the second frame by the amount of change of the rotational angle, and an impulse determined from an output value of the flexion-side biosignal sensor and an output value of the extension-side biosignal sensor until the first frame is rotated to the second frame by the amount of change of the rotational angle.

In an embodiment of the invention which solves or reduces one or more of the above-mentioned problems, the present disclosure provides the rehabilitation supporting device further including: a drive unit arranged coaxially with a center of rotation of the angle sensor, the drive unit rotating the first frame to the second frame; a torque sensor arranged coaxially with the center of rotation of the angle sensor, the torque sensor detecting a torque which rotates the first frame to the second frame; and a control unit arranged to operate the drive unit based on information acquired from the flexion-side biosignal sensor, the extension-side biosignal sensor, the angle sensor and the torque sensor, and the respective correction values acquired from the calibration unit.

In an embodiment of the invention which solves or reduces one or more of the above-mentioned problems, the present disclosure provides the rehabilitation supporting device wherein, when the joint is not in action, the control unit causes the drive unit to apply a load of a predetermined torque to the joint, and wherein the calibration unit is arranged to determine, when the flexor and the extensor respectively act to withstand the load of the predetermined torque in order to maintain a posture of the joint, the flexion-side correction value and the extension-side correction value based on respective output values of the flexion-side biosignal sensor, the extension-side biosignal sensor, and the torque sensor.

In an embodiment of the invention which solves or reduces one or more of the above-mentioned problems, the present disclosure provides the rehabilitation supporting device further including a correction unit arranged to output, to the control unit, a flexor output signal obtained from an output value of the flexion-side biosignal sensor corrected based on the flexion-side correction value, and an extensor output signal obtained from an output value of the extension-side biosignal sensor corrected based on the extension-side correction value, wherein the control unit operates the drive unit based on the flexor output signal and the extensor output signal, and the rotational angle position from the angle sensor.

In an embodiment of the invention which solves or reduces one or more of the above-mentioned problems, the present disclosure provides the rehabilitation supporting device further including: a fixture arranged to fix the first frame to the second frame at an arbitrary rotational angle; a first strain gage which is attached to the first frame and measures a bending stress applies to the first frame; and a second strain gage which is attached to the second frame and measure a bending stress applied to the second frame.

In an embodiment of the invention which solves or reduces one or more of the above-mentioned problems, the present disclosure provides the rehabilitation supporting device wherein the calibration unit determines, when the first frame is fixed to the second frame at the arbitrary rotational angle by the fixture and the flexor and the extensor act to rotate the first frame to the second frame, the flexion-side correction value and the extension-side correction value based on information acquired from the flexion-side biosignal sensor, the extension-side biosignal sensor, the first strain gage, and the second strain gage.

In an embodiment of the invention which solves or reduces one or more of the above-mentioned problems, the present disclosure provides the rehabilitation supporting device wherein the indicating unit includes a display unit arranged to display the flexor output signal, the extensor output signal, and the rotational angle position.

In an embodiment of the invention which solves or reduces one or more of the above-mentioned problems, the present disclosure provides the rehabilitation supporting device wherein the indicating unit includes a simulation unit arranged to provide visual or tangible information, the simulation unit including: a first simulation frame and a second simulation frame arranged independently of the first frame and the second frame, an end of the first simulation frame being rotatably connected to an end of the second simulation frame by a connection part; a simulation object angle sensor arranged in the connection part to detect a rotational angle position of the first simulation frame and the second simulation frame; a simulation object drive unit arranged coaxially with a center of rotation of the simulation object angle sensor, the simulation object drive unit rotating the second simulation frame to the first simulation frame; and a simulation object control part arranged to cause the simulation object drive unit to rotate the first simulation frame and the second simulation frame by converting the flexor output signal obtained from the output value of the flexion-side biosignal sensor corrected based on the flexion-side correction value, the extensor output signal obtained from the output value of the extension-side biosignal sensor corrected based on the extension-side correction value, and the rotational angle position of the angle sensor into output signals to the simulation object drive unit.

In an embodiment of the invention which solves or reduces one or more of the above-mentioned problems, the present disclosure provides the rehabilitation supporting device further including: a drive unit arranged coaxially with a center of rotation of the angle sensor, the drive unit rotating the first frame to the second frame; a torque sensor arranged coaxially with the center of rotation of the angle sensor, the torque sensor detecting a torque which rotates the first frame to the second frame; a first strain gage which is attached to the first frame and measures a bending stress applied to the first frame; a second strain gage which is attached to the second frame and measures a bending stress applied to the second frame; and a control unit arranged to operate the drive unit based on the flexor output signal, the extensor output signal, the rotational angle position of the angle sensor, a detection value of the torque sensor, a detection value of the first strain gage, and a detection value of the second strain gage.

In an embodiment of the invention which solves or reduces one or more of the above-mentioned problems, the present disclosure provides the rehabilitation supporting device wherein the control unit is arranged to operate the drive unit based on a rotational angle position of the simulation object angle sensor, and wherein the simulation object control part is arranged to operate the simulation object drive unit based on the flexor output signal, the extensor output signal, the rotational angle position of the angle sensor, the detection value of the torque sensor, the detection value of the first strain gage, and the detection value of the second strain gage.

Effects of the Invention

In the rehabilitation supporting device of one embodiment of the invention, the relative rotational angle position of the first skeletal portion and the second skeletal portion extending from the joint as the object of measurement, and the biosignals from the flexor and the extensor around the joint can be simultaneously detected as absolute quantities. Therefore, it is possible to easily determine the correlation between the motion of the joint and the biosignals from the muscles for moving the joint.

The rehabilitation supporting device of one embodiment of the invention detects simultaneously the motion of the joint and the biosignals of the flexor and the extensor which are the antagonistic muscles around the joint, and includes the calibration unit and the memory unit. Therefore, even if a detection error of the biosignals arises each time the rehabilitation supporting device is attached to the person as a living body, the flexion-side correction value of the flexion-side biosignal for the rotational angle position, and the extension-side correction value of the extension-side biosignal for the rotational angle position can be easily set up, and the motion of the joint as the object of measurement and the respective biosignals of the voluntary muscle can be output in a quantitative manner.

Figure 1:
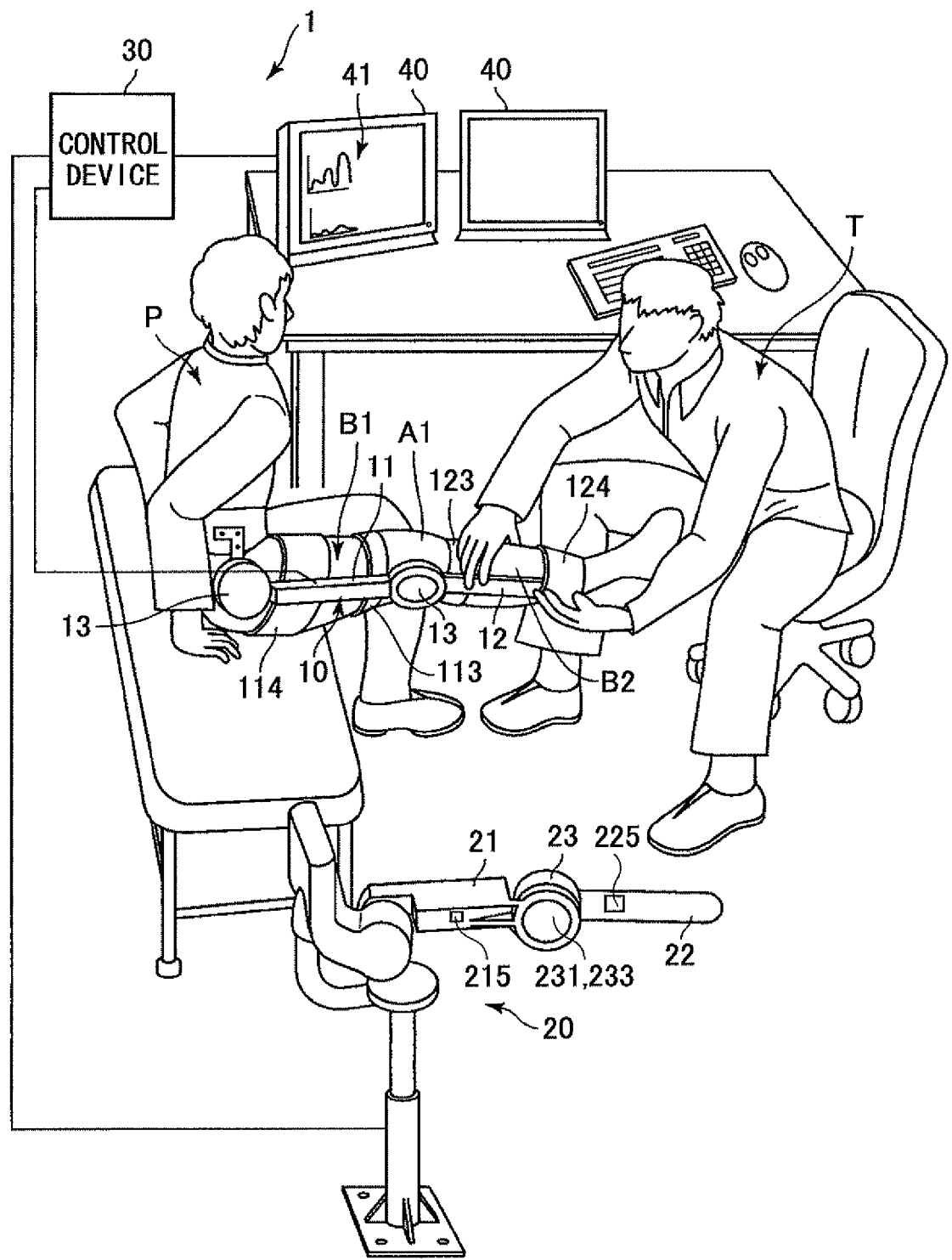
FIG. 1 is a perspective view illustrating the situation in which a rehabilitation supporting device of a first embodiment of the invention is used.

DESCRIPTION OF REFERENCE NUMERALS 1 rehabilitation supporting device,
10, 10A-10C biometric measuring device
11, 311, 411, 511 first frame
12, 312, 412, 512 second frame
14 flexion-side biosignal sensor
15 extension-side biosignal sensor
16 fixture
20 simulation unit (indicating unit)
21 first simulation frame
22 second simulation frame
23 connection part
31 calibration unit
32 control unit
33 simulation object control part
34 memory unit
35 correction unit
40 display unit (indicating unit)
115 first strain gage
125 second strain gage
131 angle sensor
132 drive unit
133 torque sensor
231 simulation object angle sensor
232 simulation object drive unit
233 simulation object torque sensor
α rotation axis (joint)
A1 knee joint (joint)
A2 hip joint (joint)
A3 elbow joint (joint)
A4 wrist joint (joint)
B1 upper thigh
B2 lower thigh
B3 upper arm part
B4 forearm part
B5 palm
P person (human body)

BEST MODE FOR CARRYING OUT THE INVENTION

A description will be given of a rehabilitation supporting device 1 of a first embodiment of the invention with reference to FIGS. 1 to 10. The rehabilitation supporting device 1 is a device which measures a motion or a physical ability of a joint as a moving part of a human body in a quantitative manner. Specifically, the rehabilitation supporting device 1 enables, before or during the rehabilitation for recovery of a motion or physical ability of a joint which is physically impaired due to illness or injury, the motion or physical ability of the joint and its voluntary muscle to be measured in a quantitative manner.

Figure 2:
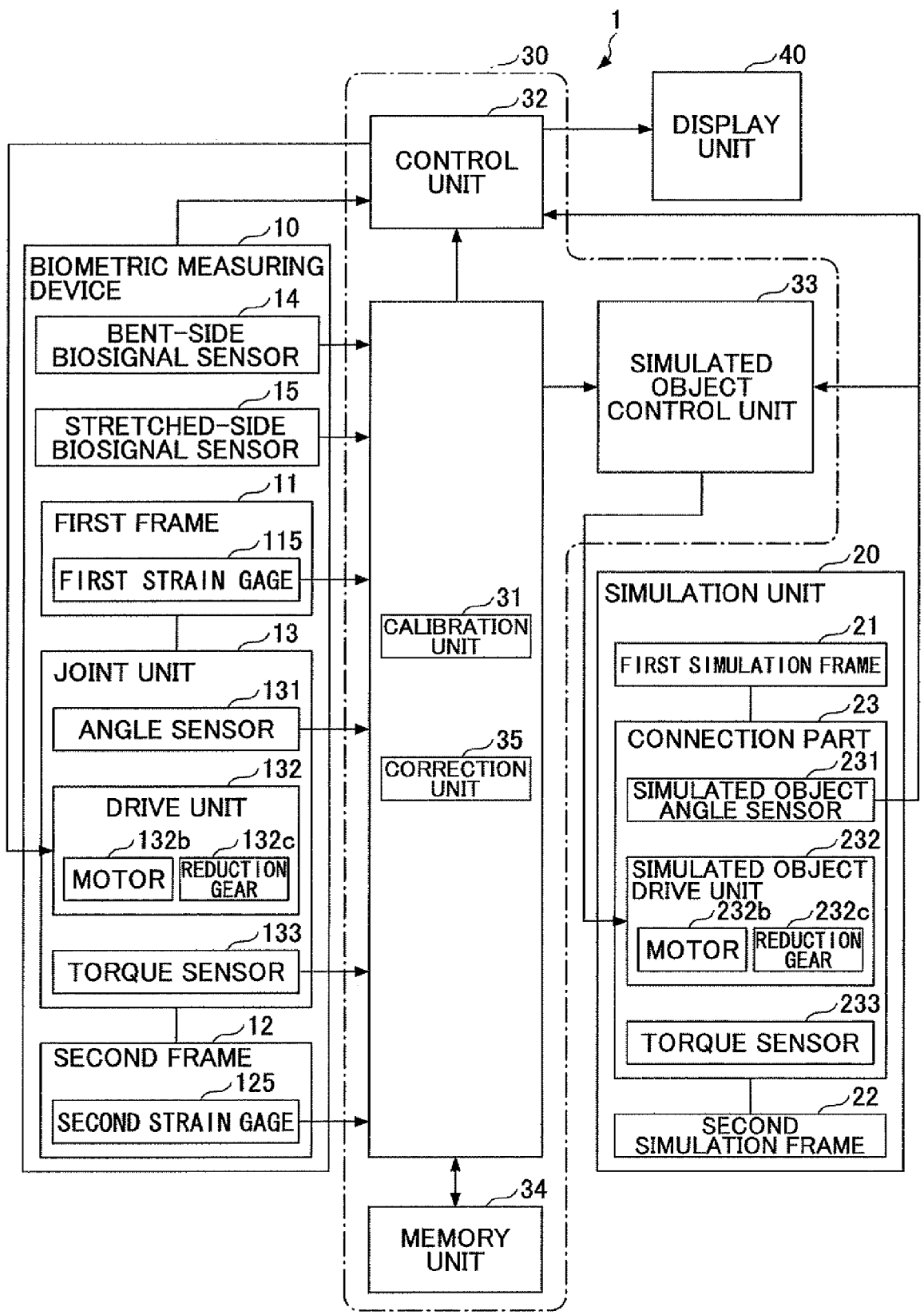
FIG. 2 is a block diagram illustrating the composition of the rehabilitation supporting device illustrated in FIG. 1.
Figure 3:
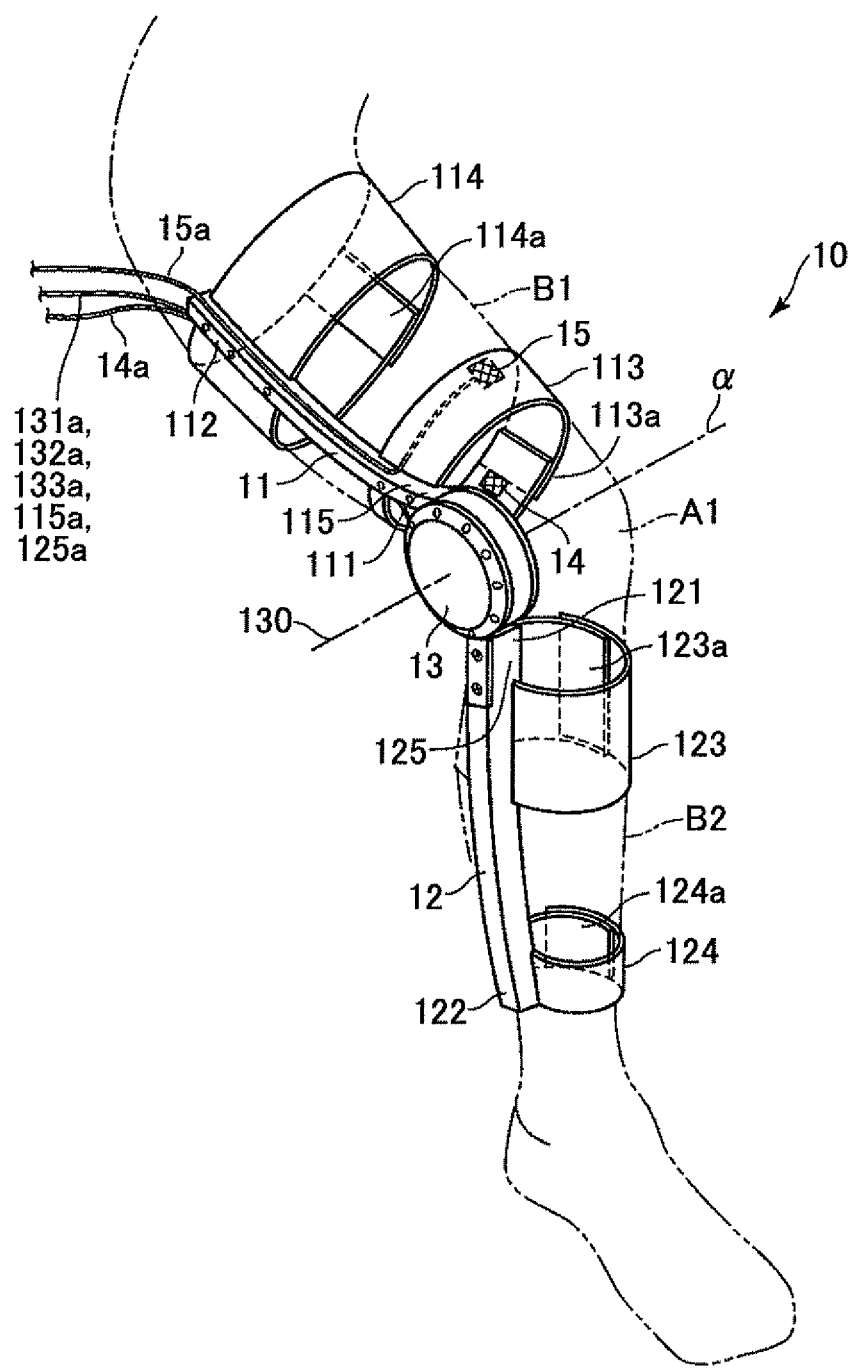
FIG. 3 is a perspective view of a biometric measuring device of the rehabilitation supporting device illustrated in FIG. 2.
Figure 4:
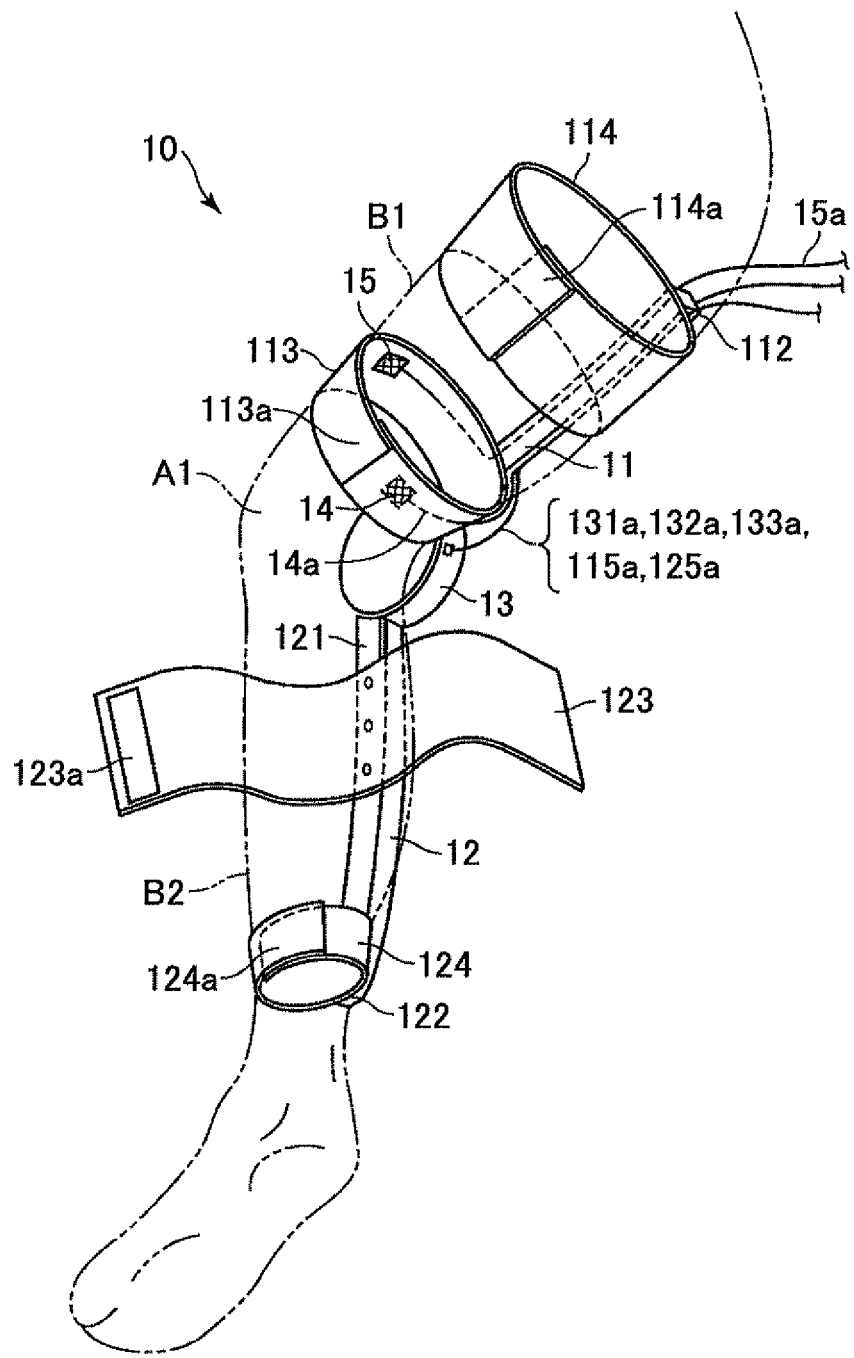
FIG. 4 is a perspective view of the biometric measuring device illustrated in FIG. 3 when viewed from the opposite side.

In the following, a case in which the rehabilitation supporting device 1 of this embodiment is applied to perform the rehabilitation of a knee joint A1 of a person P as a human body subjected to rehabilitation will be described. As illustrated in FIG. 1, the rehabilitation supporting device 1 includes a biometric measuring device 10, a simulation unit 20, a control device 30, and a display unit 40. As illustrated in FIGS. 2 to 4, the biometric measuring device 10 includes a first frame 11, a second frame 12, a joint unit 13, a flexion-side biosignal sensor 14, and an extension-side biosignal sensor 15.

As illustrated in FIGS. 3 and 4, the first frame 11 is attached to an upper thigh B1 of the person P extending along a femur as a first skeletal portion from a knee joint A1 which is the object of measurement. The first frame 11 is provided with bands 113 and 114, the band 113 disposed at a base part 111 of the first frame 11 near the knee joint A1, and the band 114 disposed at a tip part 112 of the first frame 11 distant from the knee joint A1. Each of the bands 113 and 114 is made of a flexible material having a very small elasticity. The bands 113 and 114 have surface fasteners 113a and 114a respectively so that they can be adjusted according to the size of the upper thigh B1 of the person P. A first strain gage 115 is attached to the base part 111 of the first frame 11, and a stress which acts on the first frame 11 when the knee is bent or stretched is measured by the first strain gage 115.

The second frame 12 is attached to a lower thigh B2 of the person P extending along a tibia as a second skeletal portion from the knee joint A1 in a direction opposite to the femur (the first skeletal portion). The second frame 12 is provided with bands 123 and 124, the band 123 disposed at a base part 121 of the second frame 12 near the knee joint A1, and the band 124 disposed at a tip part 122 of the second frame 12 distant from the knee joint A1. Similar to the bands 113 and 114 of the first frame 11, each of the bands 123 and 124 is made of a flexible material having very little elasticity. The bands 123 and 124 have surface fasteners 123a and 124a respectively so that they can be adjusted according to the size of the lower thigh B2 of the person P. A second strain gage 125 is attached to the base part 121 of the second frame 12, and a stress which acts on the second frame 12 when the knee is flexed or extended is measured by the second strain gage 125. Signal lines 115a and 125a of the first strain gage 115 and the second strain gage 125 are arranged along the first frame 11.

As illustrated in FIG. 3, the joint unit 13 is disposed between the first frame 11 and the second frame 12 and rotatably connects the first frame 11 and the second frame 12. A rotation center 130 of the joint unit 13 is arranged coaxially with a rotation axis α of the knee joint A1. As illustrated in FIG. 2, the joint unit 13 includes an angle sensor 131, a drive unit 132, and a torque sensor 133, which are built in the joint unit 13. The angle sensor 131 detects a relative rotational angle position between the first frame 11 and the second frame 12, and detects an amount of rotation θ. Examples of the angle sensor 131 may include a rotary encoder, a variable resistor, a variable capacitor, etc.

The drive unit 132 includes a motor 132b which generates a driving rotation force, and a reduction gear 132c which reduces the rotation speed of the output of the motor 132b. The driving rotation force of the motor is transmitted from the drive unit 132 to rotate the first frame 11 or the second frame 12 so that the relative rotational angle of the first frame 11 and the second frame 12 is changed in a direction of flexion or extension of the knee joint A1. The motor 132b can be stopped at an arbitrary rotational angle, and the rotation direction of the motor 132b can be reversed, and the rotation speed can be adjusted by the output of the motor 132b. An example of the motor 132b is a servo motor. The torque sensor 133 detects a torque which acts on the rotation center 130 of the joint unit 13 according to the output of the motor 132b. A signal line 131a of the angle sensor 131, a power cable 132a of the drive unit 132, and a signal line 133a of the torque sensor 133 are arranged along the side of the first frame 11 in the longitudinal direction, as illustrated in FIG. 4.

As illustrated in FIGS. 3 and 4, the flexion-side biosignal sensor 14 and the extension-side biosignal sensor 15 are internally arranged inside the band 113 disposed near the base part 111 of the first frame 11. Signal lines 14a and 15a of the sensors 14 and 15 are arranged along the first frame 11. The flexion-side biosignal sensor 14 is attached to the body surface corresponding to any of the semibranosus, the semitendinosus, and the biceps femoris, which mainly work as a flexor which bends the knee joint A1 between the femur and the tibia, and measures a flexion-side neurotransmission signal and a flexion-side myoelectric potential signal which constitute a biosignal. The extension-side biosignal sensor 15 is attached to the body surface corresponding to the quadriceps femoris, which mainly works as an extensor which extends the femur and the tibia around the knee joint A1, and measures an extension-side neurotransmission signal and an extension-side myoelectric potential signal which constitute a biosignal.

The flexion-side neurotransmission signal is a biosignal which is formed by a weak electric signal transmitted from the brain when flexing the knee joint A1. The flexion-side myoelectric potential signal is a biosignal which is formed by a biopotential signal transmitted from the brain when the semibranosus, the semitendinosus or the biceps femoris, works as the flexor. The extension-side neurotransmission signal is a biosignal which is formed by a weak electric signal from the brain when extending the knee joint A1. The extension-side myoelectric potential signal is a biosignal which is formed by a biopotential signal from the brain when the quadriceps femoris works as the extensor.

The amplitude of the flexion-side myoelectric potential signal or the extension-side myoelectric potential signal is relative to the strength of the muscular line activity. The amplitude of the flexion-side neurotransmission signal or the extension-side neurotransmission signal is relative to the amplitude of the flexion-side myoelectric potential signal or the extension-side myoelectric potential signal. The flexion-side neurotransmission signal and the extension-side neurotransmission signal are measured prior to the flexion-side myoelectric potential signal and the extension-side myoelectric potential signal.

That is, a series of the flexion-side neurotransmission signal and the flexion-side myoelectric potential signal, and a series of the extension-side neurotransmission signal and the extension-side myoelectric potential signal are respectively detected by the flexion-side biosignal sensor 14 and the extension-side biosignal sensor 15. In the following, for the sake of convenience, the flexion-side neurotransmission signal and the flexion-side myoelectric potential signal are collectively referred to as "flexion-side biosignal", and the extension-side neurotransmission signal and the extension-side myoelectric potential signal are collectively referred to as "extension-side biosignal".

As illustrated in FIG. 1, a simulation unit 20 is an example of an indicating unit which provides visual or tangible information. As illustrated in FIGS. 1 and 2, the simulation unit 20 includes a first simulation frame 21 and a second simulation frame 22 which are arranged independently of the first frame 11 and the second frame 12. The simulation unit 20 further includes a connection part 23 which connects the first simulation frame 21 and the second simulation frame 22 so that the frames 21 and 22 are rotatable to each other. The connection part 23 includes a simulation object angle sensor 231, a simulation object drive unit 232, and a simulation object torque sensor 233, which are built in the connection part 23.

The simulation object angle sensor 231 detects a relative rotational angle position between the first simulation frame 21 and the second simulation frame 22, and detects an amount of rotation $\phi$. Examples of the simulation object angle sensor 231 may include a rotary encoder, a variable resistor, a variable capacitor, etc.

Similar to the above-mentioned drive unit 132, the simulation object drive unit 232 includes a motor 232b and a reduction gear 232c which are built in the simulation object drive unit 232. The output shaft of the simulation object drive unit 232 is arranged coaxially with a rotation center of the simulation object angle sensor 231, and rotates the second simulation frame 22 relative to the first simulation frame 21. Similar to the motor of the drive unit 132, the motor 232b can be stopped at an arbitrary rotational angle, the rotation direction of the motor 232b can be changed to either a flexing direction or an extending direction, and the rotation speed can be freely adjusted according to the output. An example of the motor 232b is a servo motor.

The simulation unit 20 includes a strain gage 215 attached to the first simulation frame 21 and a strain gage 225 attached to the second simulation frame 22. The simulation unit 20 can measure a load which acts on the simulation unit 20 by using the simulation object torque sensor 233 of the connection part 23 and the strain gages 215 and 225 of the first simulation frame 21 and the second simulation frame 22.

The control device 30 is constituted by a computer. As illustrated in FIG. 2, the control device 30 includes a calibration unit 31, a control unit 32, a simulation object control part 33, a memory unit 34, and a correction unit 35. Respective control programs are stored beforehand in the control device 30 so that the control device 30 can perform respective control processes which are illustrated in FIG. 5, FIG. 8, FIG. 9, and FIG. 10, which will be described later.

In response to the request from the control unit 32, the calibration unit 31 reads respective measurement values of the flexion-side biosignal sensor 14, the extension-side biosignal sensor 15, the angle sensor 131, the torque sensor 133, the first strain gage 115, and the second strain gage 125, which are obtained simultaneously. The calibration unit 31 sets up respectively an individual correction value to calibrate a reference potential which varies for every person P and for every joint, a flexion-side correction value to calibrate the output value of the flexion-side biosignal sensor 14, and an extension-side correction value to correct the output value of the extension-side biosignal sensor 15. The individual correction value, the flexion-side correction value, and the extension-side correction value are set up by the calibration unit 31 which is a calibration process performed by the control unit.

The control unit 32 is constituted by a CPU (central processing unit). Based on the information acquired by using the flexion-side biosignal sensor 14, the extension-side biosignal sensor 15, the angle sensor 131, the torque sensor 133, and the simulation object angle sensor 231, and based on the flexion-side correction value and the extension-side correction value, acquired from the calibration unit 35, the control unit 32 controls the motor 132b of the drive unit 132. The signals (information) output from the flexion-side biosignal sensor 14 and the extension-side biosignal sensor 15 among the sensors of the biometric measuring device 10 are input to the calibration unit 31 and the correction unit 35. In this embodiment, the signals output from the other sensors, including the flexion-side biosignal sensor 14, the extension-side biosignal sensor 15, the first strain gage 115, the second strain gage 125, the angle sensor 131, and the torque sensor 133, are input to the calibration unit 31 and input also to the control unit 32 as information of physical quantities.

The information which is acquired by using the respective sensors is as follows. In the case of the flexion-side biosignal sensor 14 and the extension-side biosignal sensor 15, the acquired information is a biosignal which is formed by a detected biopotential signal. In the case of the angle sensor 131 and the simulation object angle sensor 231, the acquired information is a detection signal which indicates a rotational angle position, or digital data obtained by the detection signal. In the case of the torque sensor 133, the acquired information is a detection signal which indicates a torque which acts on the drive unit 132, or digital data obtained by the detection signal.

The control unit 32 uses the flexion-side neurotransmission signal component of the flexion-side biosignal included in the flexor output signal and the extension-side neurotransmission signal component of the extension-side biosignal included in the extensor output signal as a trigger signal which operates the motor 132b of the drive unit 132. Thereby, the biometric measuring device 10 which includes the drive unit 132 hardly makes the person P feel the delay relative to the motion.

Based on the flexor output signal, the extensor output signal, the rotational angle position of the angle sensor 131, and the rotational angle position of the simulation object angle sensor 231, the simulation object control part 33 controls the simulation object drive unit 232, and rotates the first simulation frame 21 and the second simulation frame 22. Similar to the control unit 32, the simulation object control part 33 uses, as a trigger signal which operates the motor 232b of the simulation object drive unit 232, the flexion-side neurotransmission signal component of the flexion-side biosignal included in the flexor output and the extension-side neurotransmission signal component of the extension-side biosignal included in the extensor output.

The memory unit 34 is a memory which is built in the control device 30, The memory unit 34 stores the flexion-side correction value and the extension-side correction value, which are set up by the calibration unit 31, and stores the individual correction values of biosignals which are different for individual persons P. The correction unit 35 corrects the output value of the flexion-side biosignal sensor 14 based on the flexion-side correction value, and corrects the output value of the extension-side biosignal sensor 15 based on the extension-side correction value. The correction unit 35 outputs a flexor output signal corrected based on the flexion-side correction value, an extensor output signal corrected based on the extension-side correction value, and the rotational angle position, respectively, to each of the control unit 32 and the simulation object control part 33.

The display unit 40 is an example of the indicating unit which provides visual information. The display unit 40 is a monitor which displays the numerical values or the graphs such as respective measured biosignals of the measurement data on the screen 41 through the control unit 32. For example, the data displayed on the screen 41 includes the output values of the flexion-side biosignal sensor 14 and the extension-side biosignal sensor 15, the rotational angle position of the angle sensor 131, the detection value of the torque sensor 133, the detected stress values of the first strain gage 115 and the second strain gage 125, the flexion-side correction value and the extension-side correction value which set up by the calibration unit 31, the individual correction value which varies for every part of the object of measurement, etc. A method of displaying the screen 41 is to set up a virtual space and display a diagram equivalent to the simulation unit 20.

The rehabilitation supporting device 1 is set up by the processes and methods illustrated in FIGS. 5 to 10, and is applied to rehabilitation. First, an initialization process which initializes an individual correction value which varies for every joint and for every person P is performed according to the control processing illustrated in FIG. 5.

In the following, a case in which the biometric measuring device 10 is attached to the right leg of the person P as illustrated in FIGS. 3 and 4 will be described.

After the biometric measuring device 10 is worn to the right leg (the knee joint A1) of the person P, operation of the biometric measuring device 10 is started if the power switch is turned ON. The operation of the biometric measuring device 10 performed at this time is to attach the flexion-side biosignal sensor 14 to the body surface (where a biosignal is easily detectable) corresponding to any of the semibranosus, the semitendinosus, and the biceps femoris (which serve as the flexor), and attach the extension-side biosignal sensor 15 to the body surface (where a biosignal is easily detectable) corresponding to the quadriceps femoris (which serves as the extensor).

The biometric measuring device 10 is arranged so that the rotation center 130 of the joint unit 13 is coaxial with the rotation axis α of the knee joint A1 of the person P, and it is fixed to the right leg of the person P by using the bands 113,114,123,124. The bands 113 and 114 attached to the first frame 11 are wound around the both ends of the thigh of the person P, so that the flexion-side biosignal sensor 14 and the extension-side biosignal sensor 15 are pressed against the flexor and the extensor of the person P, respectively.

Figure 5:
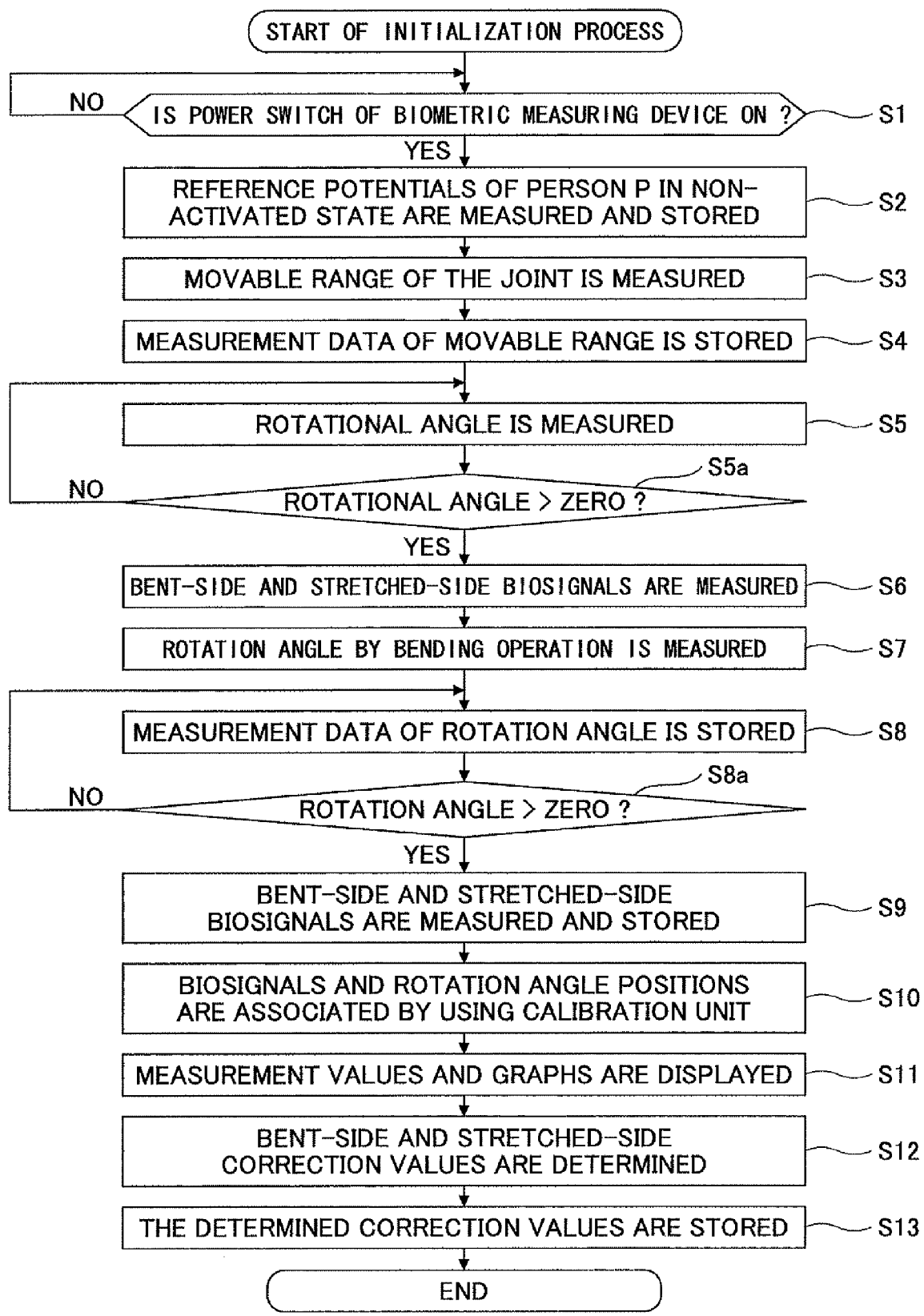
FIG. 5 is a flowchart for explaining an initialization process performed by the rehabilitation supporting device illustrated in FIG. 2.

Upon start of the initialization process of FIG. 5, the control device 30 detects whether the power switch of the biometric measuring device 10 is turned ON (S1). When it is detected in step S1 that the power switch of the biometric measuring device 10 is ON, the control process proceeds to step S2.

Subsequently, a flexion-side reference potential (biosignal) and an extension-side reference potential (biosignal) of the person P when the person P sits on a chair in a non-activated state where the flexor and the extensor are not in action are measured by the flexion-side biosignal sensor 14 and the extension-side biosignal sensor 15, respectively, and the measured flexion-side and extension-side reference potentials are stored in the memory unit 34 (S2).

Subsequently, the person P is in the non-activated state and the knee joint A1 of the person P is moved passively with the help of an instructor T of rehabilitation, such as a doctor or a physiotherapist. The movable range of the knee joint A1 is measured using the angle sensor 131 of the joint unit 13 (S3). The movable range is measured based on the flexion-side and extension-side side rotational angle positions measured by the angle sensor 131, and the measurement data of the movable range is stored in the memory unit 34 (S4).

This movable range is a range in which the joint may be rotated according to the pliability of the knee joint A1 without exerting the muscular force, and differs from the operating range in which the joint may be actively moved according to the muscular force. This movable range is measured in order to ensure that the tendon or the muscle are not hurt during the rehabilitation which will be performed later.

Figure 6:
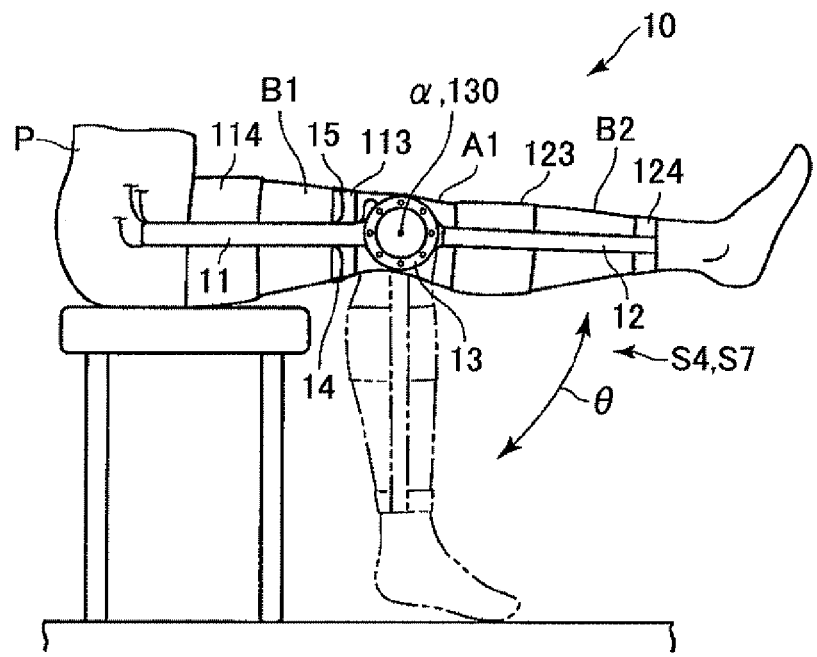
FIG. 6 is a side view illustrating the state of measuring a dynamic biosignal using the biometric measuring device illustrated in FIG. 3.

When measuring the movable range of the knee joint A1, the person P performs stretching operation which flings up the lower thigh B2 with his own intention as illustrated in FIG. 6. If the movable range is very narrow due to decline in muscular force or shrinking movable range due to muscular atrophy or if the joint hardly moves due to the physical disability of the person, the muscular force is measured within the movable range.

If the extensor works by the intention of the person P, the knee joint A1 will be stretched. When the knee joint A1 is stretched, the rotational angle of the knee joint A1 is measured by the angle sensor 131 (S5) simultaneously. Then, it is detected in step S5a whether the rotational angle measured by the angle sensor 131 is larger than zero. When the rotational angle measured by the angle sensor 131 is larger than zero, the control process proceeds to step S6. In step S6, the amount of change of the rotational angle is measured and the flexion-side biosignal and the extension-side biosignal (potential signals) are measured by the flexion-side biosignal sensor 14 and the extension-side biosignal sensor 15.

Subsequently, the person P performs a bending operation of the knee joint A1 by his intention. For example, when it is difficult for the person P to bend the knee joint A1 with the posture in which he sits down on the chair, the person P may lie on his stomach on a bed and raise the lower thigh B2. Alternatively, the person P may stand straight and raise the lower thigh B2. Then, similar to the case of stretching operation, the muscular force is measured within the movable range of the knee joint A1, and the amount of change of the rotational angle position at this time is measured by the angle sensor 131 (S7). The rotational angle measured by the angle sensor 131 is stored in the memory unit 34 (S8).

Subsequently, it is detected in step S8a whether the rotational angle measured by the angle sensor 131 is larger than zero. When it is detected in step S8a that the rotational angle measured by the angle sensor 131 is larger than zero, the control process proceeds to step S9. In step S9, the flexion-side biosignal and the extension-side biosignal (potential signals) are measured by the flexion-side biosignal sensor 14 and the extension-side biosignal sensor 15, and the rotational angle position and the biosignals of the extensor and the flexor, acquired by the bending operation, are stored in the memory unit 34.

Subsequently, by using the calibration unit 31, the measurement value of each biosignal and the rotational angle position when the measurement value is obtained are associated (S10). Each measurement value is output to the display unit 40, and the numerical values or graphs are displayed on the screen 41 (S11). By checking the measurement value in the screen 41 displayed on the display unit 40, the instructor T can immediately determine whether the flexion-side biosignal sensor 14 and the extension-side biosignal sensor 15 are respectively attached to the positions corresponding to the flexor and the extensor, and determine whether the measurement data obtained from the attachment positions shows a sufficient value as a biosignal.

At this time, a more exact correlation can be obtained by applying further the correction values considering the influence of the weight of the second frame 12 and the correction values considering the influence of gravity which acts on the lower thigh B2. As a result of the above-mentioned correlation, the calibration unit 31 determines the correlation between the rotational angle position, the flexion-side biosignal, and the extension-side biosignal. The calibration unit 31 determines the flexion-side operation correction value and the extension-side operation correction value, based on the amount of change of the rotational angle detected by the angle sensor 131, the time for the first frame 11 and the second frame 12 being rotated by the amount of change of the rotational angle, and the impulse determined from the output values of the flexion-side biosignal sensor 14 and the extension-side biosignal sensor 15 until the frames are rotated by the amount of change of the rotational angle (S12). Subsequently, the flexion-side operation correction value and the extension-side operation correction value, determined in step S12, are stored in the memory unit 34 (S13). The flexion-side operation correction value is a part of the flexion-side correction value, and the extension-side operation correction value is a part of the extension-side correction value. Then, the initialization process is completed.

After the above-mentioned initialization process is completed, an output adjustment process is performed. In the output adjustment process, the relationship between the extension-side or flexion-side muscular force and the corresponding biosignal of the person P is measured, and an output adjustment of the biosignal when the maximum muscular force is exerted is performed. Moreover, the biosignal when the muscular force is exerted to withstand the gradually applied load is measured. The above-mentioned initialization process and the output adjustment process are performed every time the biometric measuring device 10 is attached to the person P.

Figure 7:
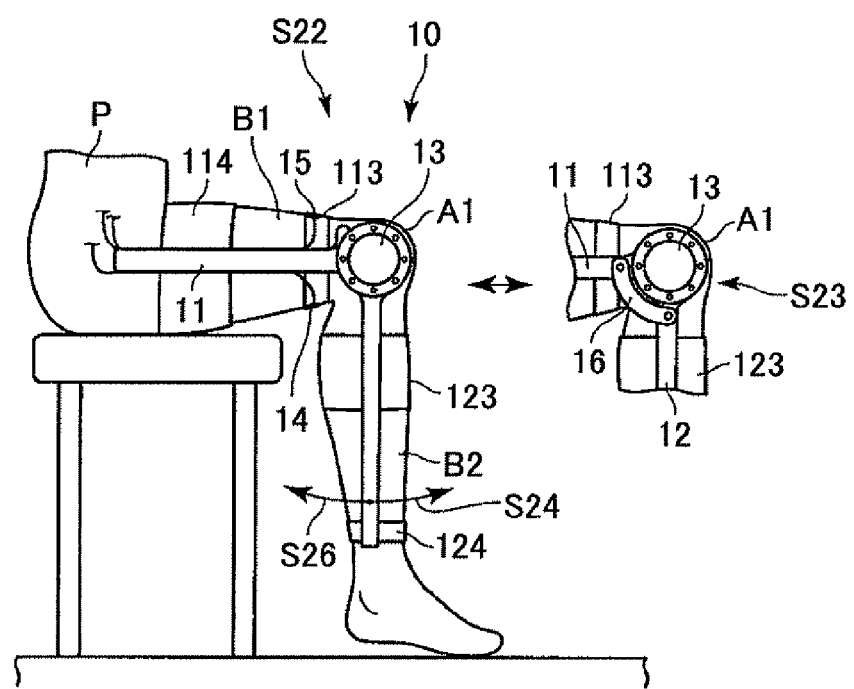
FIG. 7 is a side view illustrating the state of measuring a static biosignal using the biometric measuring device illustrated in FIG. 3.
Figure 8:
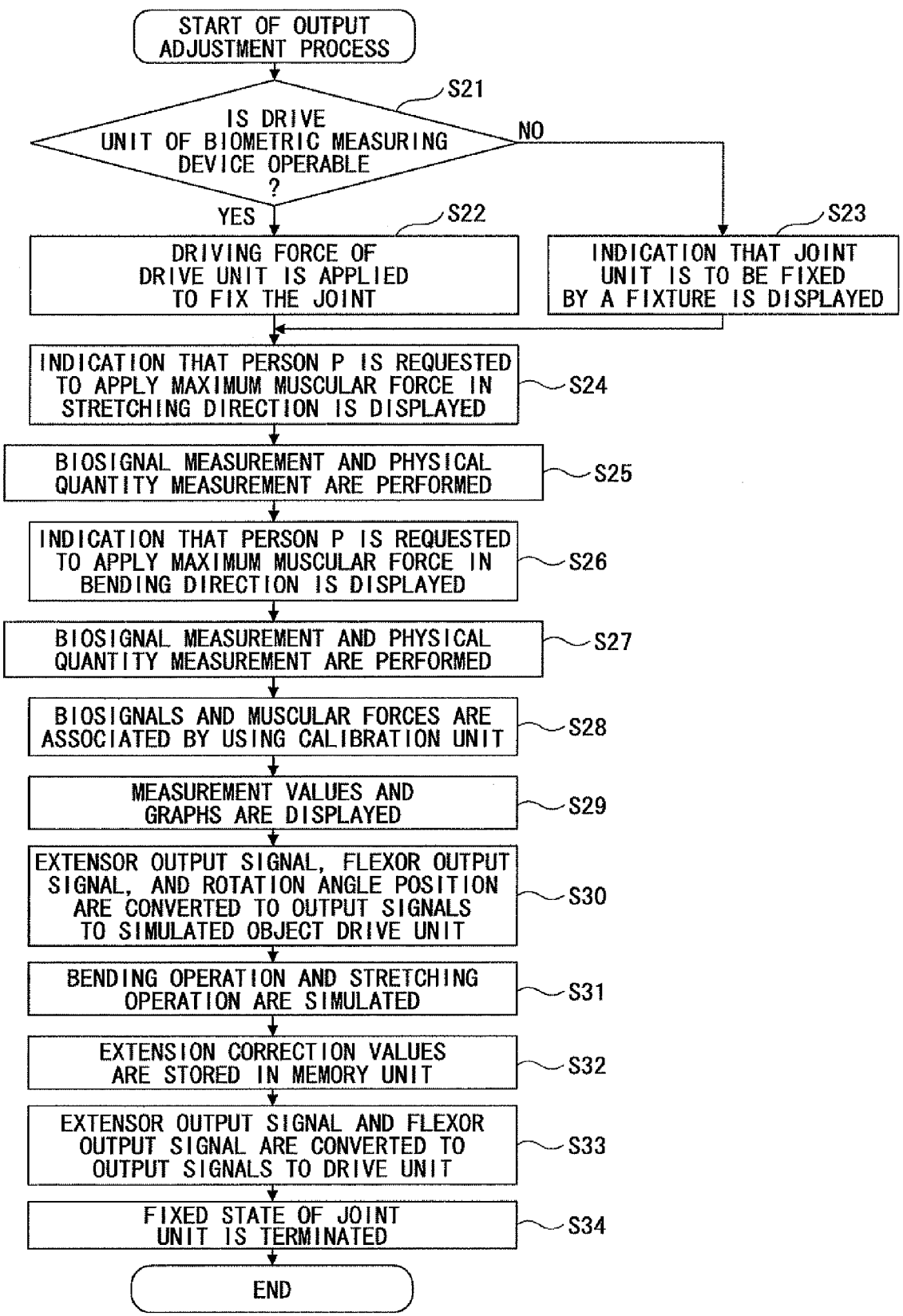
FIG. 8 is a flowchart for explaining a process of output adjustment of a muscular force relative to a biosignal using the rehabilitation supporting device illustrated in FIG. 2.

As illustrated in FIG. 7, the relative angle between the first frame 11 and the second frame 12 is fixed to a certain angle in the middle of the movable range of the joint, and, in this state, the output adjustment process is performed according to the flowchart illustrated in FIG. 8. In the state illustrated in FIG. 7, the knee joint A1 is bent to an almost right-angle. However, the relation with the rotational angle position is determined as a result of the above initialization process. When the movable range of the joint is narrow due to the shrinking of the muscle fiber, or when the range in which the muscular force can be exerted is restricted, the output adjustment process may be performed in the state other than illustrated in FIG. 7.

Upon start of the output adjustment process of FIG. 8, the control device 30 detects whether the drive unit 132 of the biometric measuring device 10 connected to the rehabilitation supporting device 1 is operable (S21). When it is detected in step S21 that the drive unit 132 is operable, the relative angle between the first frame 11 and the second frame 12 is fixed by applying a driving force of the motor 132b of the drive unit 132 (S22).

When it is detected in step S21 that the drive unit 132 is not operable, an indication that a separately prepared fixture 16 is to be used to restrain the joint unit 13, so that the relative angle between the first frame 11 and the second frame 12 does not change, is displayed on the display unit 40 (S23).

When the fixture 16 is used to fix the first frame 11 and the second frame 12, it is necessary to correct beforehand the relationship between the load applied to the joint unit 13 in the bending or stretching direction and the output values of the first strain gage 115 and the second strain gage 125.

An indication that the person P is requested to apply the maximum muscular force in the stretching direction in this state is displayed on the display unit 40 (S24). Each biosignal is measured by the flexion-side biosignal sensor 14 and the extension-side biosignal sensor 15 at this time Moreover, the torque, the rotational angle position, the stress acting on the first frame 11, and the stress acting on the second frame 12 are respectively measured as the physical quantities of the joint (S25). The torque is measured by the torque sensor 133 attached to the rotation axis of drive unit 132. The rotational angle position is measured by the angle sensor 131. The stress acting on the first frame 11 is measured by the first strain gage 115, and the stress acting on the second frame 12 is measured by the second strain gage 125.

Subsequently, an indication that the person P is requested to apply the maximum muscular force in the bending direction in the same state is displayed on the display unit 40 (S26). Also at this time, each biosignal is measured by the flexion-side biosignal sensor 14 and the extension-side biosignal sensor 15. Moreover, the torque, the rotational angle position, the stress acting on the first frame 11, and the stress acting on the second frame 12 are respectively measured as the physical quantities of the joint (S27). The torques and stresses measured by the stretching operation and the bending operation are converted into the data of the muscular force which is exerted by the knee joint A1 as the object of measurement.

When the drive unit 132 is not operable, the first frame 11 and the second frame 12 are fixed together by the fixture 16. Therefore, if the relationship between the external force and the stress values of the first strain gage 115 and the second strain gage 125 in the state where the first frame 11 and the second frame 12 are fixed together is measured beforehand, the value of the muscular force to stretch or bend the joint can be determined by measuring the stress values of the first strain gage 115 and the second strain gage 125.

The biosignals and the physical quantities around the joint are associated with each other, and the measurement data of the muscular force derived from the physical quantities are associated with the physical quantities by using the calibration unit 31 (S28). The biosignals, the physical quantities, and the measurement data of the muscular force are stored in the memory unit 34 respectively, and they are output to the display unit 40 through the control unit 32 so that the numerical values or graphs are displayed on the screen 41 of the display unit 40 (S29). By visualizing the biosignals, the physical quantities of the joint, and the muscular force by the numerical values or graphs in a quantitative manner, the relationship between the intention of the person P and the actual muscular force acting can be recognized. Thus, it is possible to intensify the communication between the instructor T and the person P.

In the above step S28, the flexion-side output correction value which associates the flexion-side biosignal and the flexion-side muscular force, and the extension-side output correction value which associates the extension-side biosignal and the extension-side muscular force are determined by the calibration unit 31. The determined correction values are stored in the memory unit 34. The flexion-side output correction value is a part of the flexion-side correction value and used in combination with the flexion-side operation correction value. The extension-side output correction value is a part of the extension-side correction value and is used in combination with the extension-side operation correction value.

Subsequently, in step S30, by using the simulation object control part 33 of the simulation unit 20 (which is an indicating unit which provides visual or tangible information), the flexor output signal which is obtained by the flexion-side correction value added to the output value of the flexion-side biosignal sensor 14, the extensor output signal which is obtained by the extension-side correction value added to the output value of the extension-side biosignal sensor 15, and the rotational angle position of the angle sensor 131 are converted into output signals to the simulation object drive unit 232.

The simulation unit 20 is arranged to simulate the action of the person P so that the simulation unit 20 is synchronized with the action of the person P and moves with the amount of rotation φ and the rotation speed which are the same as those when the person P moves the knee joint A1 within the movable range. In this state, the actual bending operation and stretching operation of the knee joint A1 of the person P are simulation by the simulation unit 20 (S31). In this manner, by actually moving the simulation unit 20 according to the muscular force of the person P, the relationship between the biosignal of the voluntary muscle which moves the joint and the corresponding operation can be easily recognized, and it is possible to easily determine the operation plan of rehabilitation, its content, and the degree of recovery through the communication between the person P and the instructor T.

When the movable range of the knee joint A1 includes a margin to the operating range in which the person P can move with his muscular force, an extension-side extension correction value and a flexion-side extension correction value are added such that the movable range of the knee joint A1 is not exceeded even with an error of the biosignal, and the amount of rotation φ of the simulation unit 20 is extended. The extension-side extension correction value and the flexion-side extension correction value are stored in the memory unit 34 (S32).

If the correlation between the biosignal and the action of the person P can be set up by the simulation unit 20, the extensor output signal and the flexor output signal are converted into the output signals to the drive unit 132 (S33). At this time, the flexion-side extension correction value and the extension-side extension correction value may be included. Finally, the fixed state of the drive unit 132 is terminated and the fixed state of the joint unit 13 is terminated (S34). When the fixture 16 is used, the fixture 16 is removed by manual operation.

Figure 9:
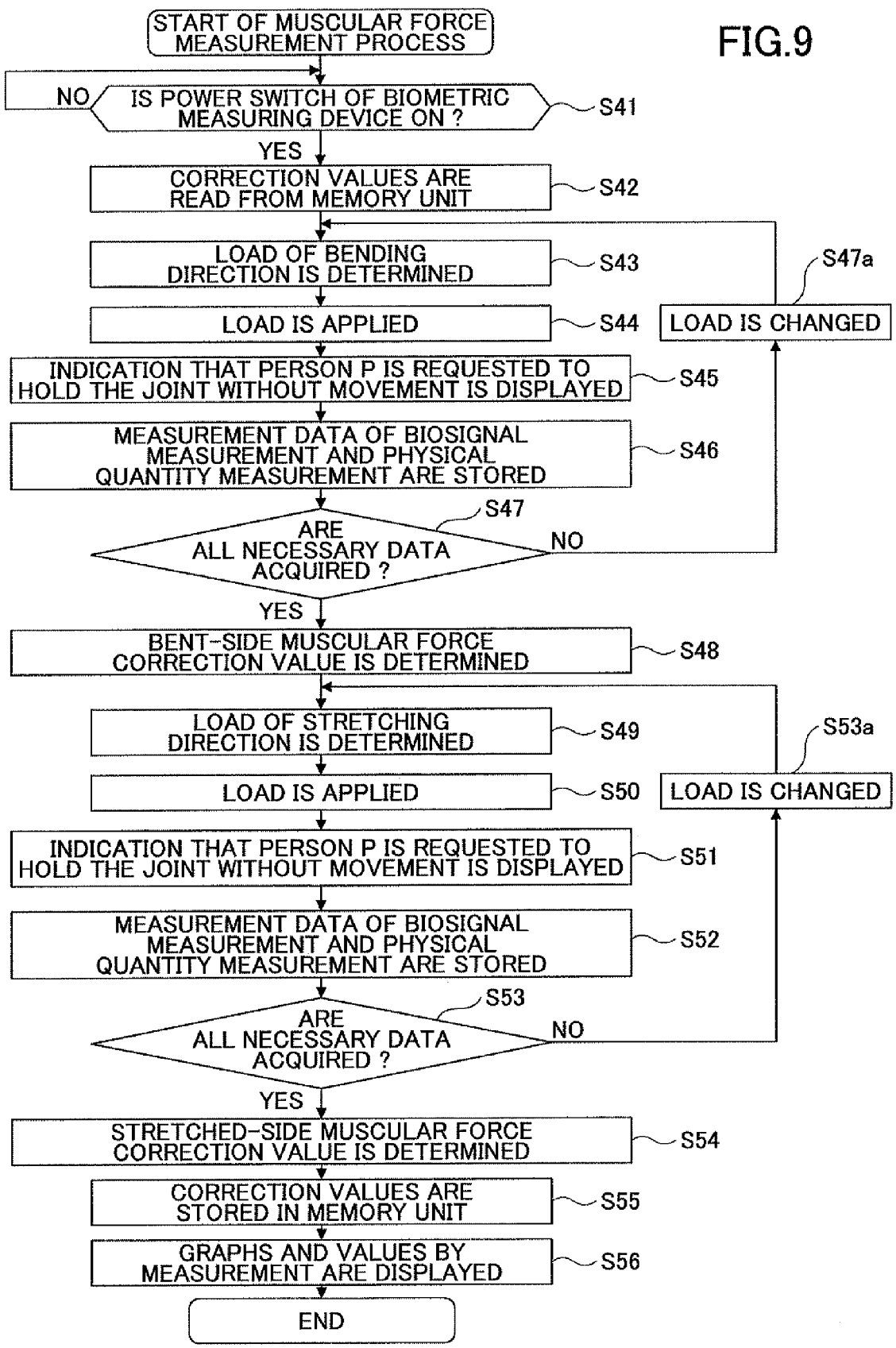
FIG. 9 is a flowchart for explaining a measurement process which measures the correlation of a biosignal relative to a muscular force using the rehabilitation supporting device illustrated in FIG. 2.

Next, the control device 30 performs a muscular force measurement process in which each muscular force at the joint as the object of measurement for two or more steps of load in the stretching direction and the bending direction, according to the flowchart illustrated in FIG. 9.

Upon start of the muscular force measurement process of FIG. 9, the control device 30 detects whether the power switch of the biometric measuring device 10 is turned ON (S41). When it is detected in step S41 that the power switch in the biometric measuring device 10 is turned ON, the control process proceeds to step S42. It is preferred to use the drive unit 132 as a means for applying a load. Alternatively, a weight or a spring force may be used to apply a load. If the control is at a point after the initialization and output adjustment processes are completed, the control immediately process proceeds to the measurement process.

The correction values to the biosignal of the person P are read from the memory unit 34 (S42). Subsequently, the load of the bending direction is determined based on the flexion-side operation correction value and the flexion-side output correction value read from the memory unit 34 (S43).

Subsequently, the motor 132b of the drive unit 132 is driven to apply the load to the knee joint A1 (S44). An indication that the person P is requested to hold the knee joint A1 so that the knee joint A1 may not move to the load applied from the drive unit 132 is displayed on the display unit 40 (545). The measurement data of each of the extension-side biosignal and the flexion-side biosignal, the torque detected by the torque sensor 133, the rotation angular position detected by the angle sensor 131, the stress detected by the first strain gage 115, and the stress detected by the second strain gage 125 are read, and the respective data are stored in the memory unit 34 (S46).

Subsequently, it is detected whether the necessary data when two or more steps of load based on the flexion-side output correction value are given are acquired (S47). When all the necessary data are not acquired, there is a possibility that the applied load is too small, and the control process proceeds to step S47a. In step S47a, the applied load is changed and the procedure of S43-S47 is again performed so that the load applied by the drive unit 132 is gradually increased.

When it is detected in step S47 that the necessary data about the flexion-side are acquired, the flexion-side muscular force correction value with respect to the relationship between the flexion-side muscular force and the biosignal is determined by the calibration unit 31 (S48).

After the flexion-side muscular force correction value is determined in step S48, the load of the stretching direction is determined based on the extension-side operation correction value and the extension-side output correction value (S49). Subsequently, the motor 132b of the drive unit 132 is driven to apply the load to the knee joint A1 (S50).

An indication that the person P is requested to hold the knee joint A1 so that the knee joint A1 may not move to the applied load is displayed on the display unit (S51). The measurement data of each of the extension-side biosignal and the flexion-side biosignal, the torque detected by the torque sensor 133, the rotation angular position detected by the angle sensor 131, the stress detected by the first strain gage 115, and the stress detected by the second strain gage 125 are read, and the respective data are stored in the memory unit 34 (S52).

Subsequently, it is detected whether the necessary data when two or more steps of load based on the extension-side output correction value are given are acquired (S53). When all the necessary data are not acquired, there is a possibility that the applied load is too small, and the control process proceeds to step S53a. In step S53a, the applied load is changed and the procedure of S49-S53 is again performed so that the load applied by the drive unit 132 is gradually increased.

When it is detected in the step S53 that all the necessary data about the extension-side are acquired, the extension-side muscular force correction value with respect to the relationship between the extension-side muscular force and the biosignal is determined by the calibration unit 31 (S54).

The flexion-side muscular force correction value and the extension-side muscular force correction value, determined in the steps S48 and S54, are stored in the memory unit 34 (S55). The numerical values or graphs of the steps of load on the bent side, the steps of load on the stretched side, the flexion-side biosignal, and the extension-side biosignal are created and the numerical values or graphs are displayed on the display unit 40 (S56). The flexion-side muscular force correction value is a part of the flexion-side correction value, and the extension-side muscular force correction value is a part of the extension-side correction value.

As described above, the rehabilitation supporting device 1 of this embodiment is arranged so that the biometric measuring device 10 is attached to the joint (for example, the knee joint A1) which is the object of rehabilitation, and it is possible to measure the correlation between the biosignal and the muscular force and the correlation between the biosignal and the rotational angle position on the stretched side or the bent side by easy operation. The rehabilitation supporting device 1 of this embodiment can perform the measurement with the correlation between the physical quantities, such as the movable range of the joint or the muscular force of the voluntary muscles, of the person P on which the rehabilitation is performed, and the biosignals being retained, and can output the measurement result in a quantitative manner. In this embodiment, the display unit 40 which provides visual information and the simulation unit 20 which provides visual or tangible information are provided as the indicating unit, and the information about the muscular force and feeling of the person P can exactly be recognized by the instructor T performing rehabilitation, such as a doctor, a physiotherapist, etc.

Next, the rehabilitation process using the simulation unit 20 will be described with reference to FIG. 10.

Figure 10:
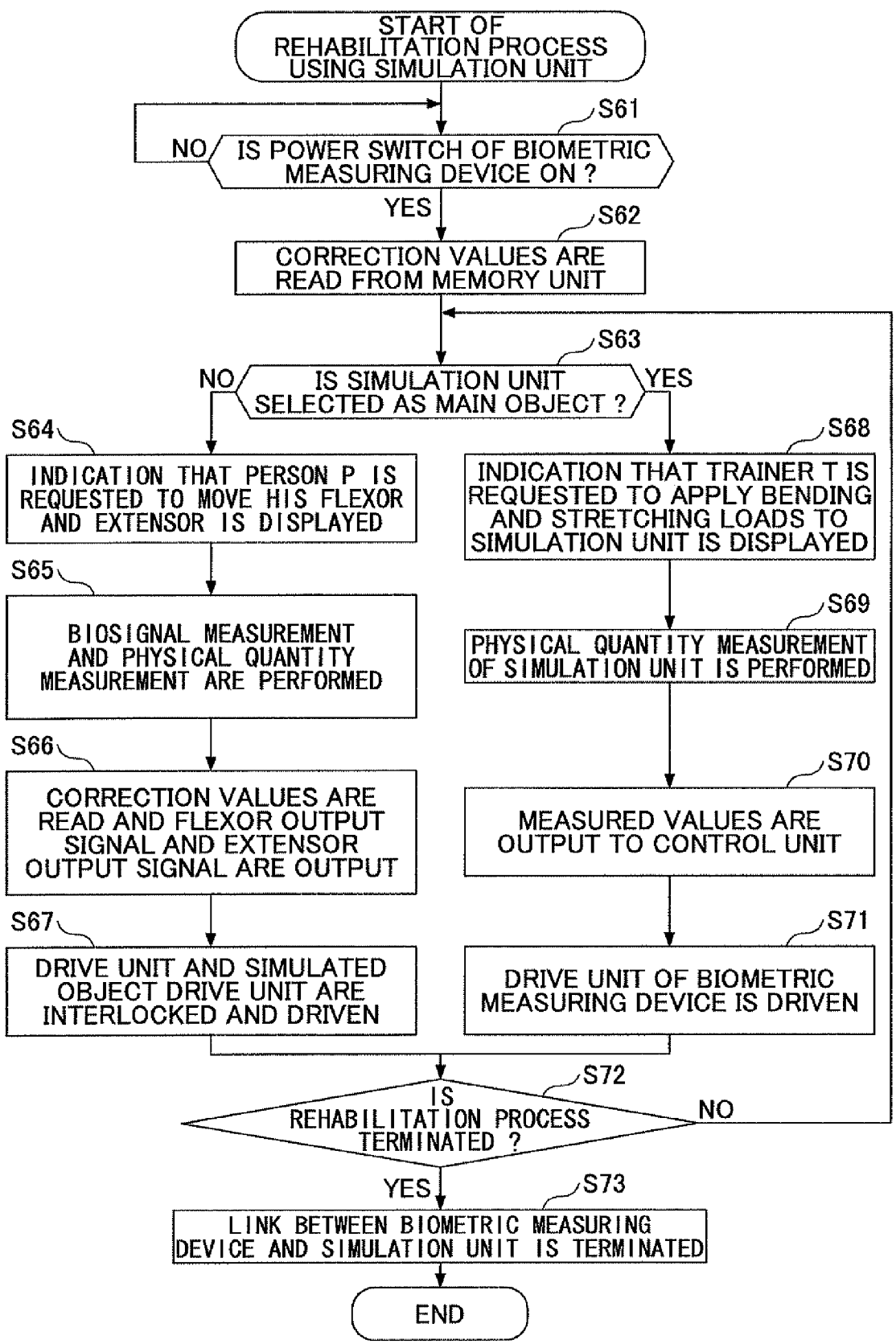
FIG. 10 is a flowchart for explaining a rehabilitation process performed by the rehabilitation supporting device using a simulation unit illustrated in FIG. 2.

Upon start of the rehabilitation process of FIG. 10, the control device 30 detects whether the power switch of the biometric measuring device 10 is turned ON (S61). When it is detected in step S61 that the power switch of the biometric measuring device 10 is turned ON, the control process proceeds to step S62.

Because the flexion-side output correction value and the extension-side output correction value are set up by the output adjustment process mentioned above, the approximation compensation of the measured muscular force of the person P may be performed by comparison with the previous measurement data. After the initialization process and the output adjustment process are performed, the reference biosignal, the flexion-side correction value, the extension-side correction value, the flexion-side extension correction value, and the extension-side extension correction value are read from the memory unit 34 as the previous correction values, and the comparison and re-setting processes are performed (S62). The rehabilitation may be started by operating the simulation unit 20 using the respective correction values stored beforehand in the memory unit 34, to confirm the operation.

As illustrated in FIGS. 1 and 2, the simulation unit 20 includes the connection part 23 in which the angle sensor 231 and the simulation object torque sensor 233 are disposed, and the first simulation frame 21 and the second simulation frame 22 in which the strain gages 215 and 225 are disposed. The torques and the stresses which are detected by these sensors are fed back to the control unit 32 and the simulation object control part 33 of the control device 30, and reflected in operation of the drive unit 132 of the biometric measuring device 10 and the simulation object drive unit 232 of the simulation unit 20.

When the simulation unit 20 is linked to the biometric measuring device 10 which is attached to the person P, the person P is requested to choose one of the option that the simulation unit 20 is used as the main object and the option that the biometric measuring device 10 is used as the main object (S63). When the option that the biometric measuring device 10 is used as the main object is chosen in step S63, the control process proceeds to step S64. In step S64, an indication that the person P is requested to apply power to the flexor and the extensor at the knee joint A1 to move the knee joint A1 is displayed on the display unit 40.

Subsequently, the measurement data of each of the torque detected by the torque sensor 133 of the biometric measuring device 10, the rotational angle position detected by the angle sensor 131, the stress detected by the first strain gage 115, and the stress detected by the second strain gage 125 are read, the biosignal measurement on the bent side and the stretched side and the physical quantity measurement are performed, and the respective measurement data are stored in the memory unit 34 (S65).

Based on the correction values read from the memory unit 34 by the correction unit 35 and the respective measurement data values measured in the step S65, the extensor output signal and the flexor output signal are output to the control unit 32 and the simulation object control part 33 (S66).

The motor 132b of the drive unit 132 is controlled by a driving signal output from the control unit 32, and the motor 232b of the simulation object drive unit 232 is controlled by the simulation object control part 33, such that the drive unit 132 and the simulation object drive unit 232 are interlocked and driven (S67).

On the other hand, when the option that the simulation unit 20 is used as the main object is chosen in the step S63, an indication that the instructor T of rehabilitation is requested to apply load to flex or extend the simulation unit 20 is displayed on the display unit 40 (S68).

The rotational angle position detected by the simulation object angle sensor 231, the torque detected by the simulation object torque sensor 233 at the connection part 23, and the stress values detected by the strain gages 215 and 225 of the first simulation frame 21 and the second simulation frame 22 are read, and the physical quantities of the simulation unit 20 are measured (S69).

Subsequently, the torque and stress values and the amount of rotational angle, measured in the step S69, are output to the control unit 32 as the external force and the amount of movement, respectively (S70). Subsequently, the motor 132b is driven according to a driving signal output to the drive unit 132 of the biometric measuring device 10 by the control device 30 based on the flexor output signal, the extensor output signal and the result of adding the external force, received from the simulation unit 20, to the flexor output signal and the extensor output signal, such that the biometric measuring device 10 is interlocked with the simulation unit 20 (S71).

As a result, the person P feels as if the bending or stretching force was applied to the knee joint A1 by the instructor T because the biometric measuring device 10 is interlocked with the simulation unit 20. The instructor T can feel the force which is applied by the person P by touching the simulation unit 20 interlocked with the operation of the person P to move the knee joint A1. The rehabilitation supporting device 1 of this embodiment is arranged so that the biometric measuring device 10 and the simulation unit 20 are interlocked with each other to form a bilateral servo system.

Subsequently, it is detected in step S72 whether the rehabilitation process is terminated. When it is detected in step S72 that the rehabilitation process is not terminated, the control is transferred to the above step S63 and the procedure of S63-S71 is repeated. On the other hand, when it is detected in step S72 that the rehabilitation process is terminated, the control is transferred to the next step S73, and the link between the biometric measuring device 10 and the simulation unit 20 is disconnected (S73).

Because the rehabilitation supporting device 1 is arranged to determine a correlation between the biosignal, the muscular force and the rotational angle of the joint and output the correlation in a quantitative manner, it is possible to construct a bilateral servo system. This bilateral servo system is a system in which both the position information and the force information are transmitted. In the bilateral system, when the two devices are linked together and share both the position information and the force information, one of the two devices can be operated by the other device, and the force applied to one of the two devices can be recognized on the side of the other device.

If a time difference does not arise by a bi-directional communication, the biometric measuring device 10 and the simulation unit 20 may be separated apart. By using a network, such as the Internet, the rehabilitation supporting device 1 may be arranged so that the biometric measuring device 10 and the simulation unit 20 are connected via the network. In this case, the condition of a physically impaired person P who is located at a remote place can be checked with the simulation unit 20.

Furthermore, the rehabilitation supporting device 1 of this embodiment may be used as follow. For example, when the muscular force of the leg has declined, the correlation between the muscular force of the leg of the person P and the biosignal is determined by the biometric measuring device 10 including the drive unit 132. Furthermore, an assist value to amplify the motor output of the drive unit 132 is added to the flexor output signal and the extensor output signal respectively so that the decline in the muscular force of the leg of the person P may be compensated for. As a result, the insufficient muscular force of the person P is compensated for by the driving force of the drive unit 132, and the person P will be able to walk without support of another person. If an exercise program in which the assist value is gradually decreased as the muscular force of the person P is recovered is set up, it is possible for the person P to perform rehabilitation while performing a daily life.

When the muscular force of the person P declines and the movable range of the joint is small because a fractured bone is restrained by a cast, the biometric measuring device 10 comprising the drive unit 132 is used, an assist value is included, and further the flexion-side extension correction value and the extension-side extension correction value, which set up the amount of rotation 8 of the biometric measuring device 10, are included in order to slightly exceed the movable range of the joint. In this way, the person P can extend the movable range of the joint while checking the situation according to his intention.

Alternatively, the rehabilitation supporting device 1 of this embodiment may be arranged to apply the load from the drive unit 132 which negates the flexor output signal and the extensor output signal, instead of applying an assist value to the biometric measuring device 10. This makes it possible to strengthen positively the muscular force of the person P which has declined.

In this manner, the rehabilitation supporting device 1 of this embodiment can output the biosignal and the muscular force in a quantitative manner by taking the correlation between the physical quantities at the joint as the object of measurement and the biosignal of the voluntary muscle at the joint. By using the indicating unit, such as the display unit 40 and the simulation unit 20, which provides visual and tangible information using the correlation, it is possible to intensify the communication between the person P and the instructor T, and the feeling of the muscles or the joint of the person P can be easily conveyed to the instructor T. Even when it is difficult for the person P to express the feeling quantitatively, the instructor T can recognize exactly the state of the disabled part of the person P by using the simulation unit 20 linked to the biometric measuring device 10.

The rehabilitation supporting device 1 of this embodiment is attached to the joint of the person P who is subjected to rehabilitation, and measures the biosignal of the voluntary muscle at the joint. The drive unit 132 of the biometric measuring device 10 can perform supporting operation based on the correlation between the biosignals and the physical quantities around the joint. Therefore, even if the person P has a physical disability in a neurotransmission system from the brain, due to damage to the cervical vertebrae or the spinal column, it is possible to use a neurotransmission signal arising in another bodily part when the joint as the object of rehabilitation is moved, as a trigger of a voluntary muscle, in order to activate the voluntary muscle.

Next, the cases in which the rehabilitation supporting device 1 is applied to joints other than the knee-joint A1 will be described.

The composition of the rehabilitation supporting device 1 of each of the following embodiments is essentially the same as the composition of the rehabilitation supporting device 1 of the first embodiment illustrating in FIG. 2. In the following embodiments, the elements which are the same as corresponding elements in FIG. 2 are designated by the same reference numerals, and a description thereof will be omitted. Because the control device 30 and the simulation unit 20 are the same as the first embodiment, a description thereof will be omitted in the following embodiments.

Next, a biometric measuring device 10A of a rehabilitation supporting device 1 of a second embodiment of the invention will be described with reference to FIGS. 11 to 13.

This biometric measuring device 10A is arranged for stretching operation and bending operation of a hip joint A2. Therefore, the measurement with respect to medial rotation, lateral rotation, adduction, and abduction is not permitted.

Figure 11:
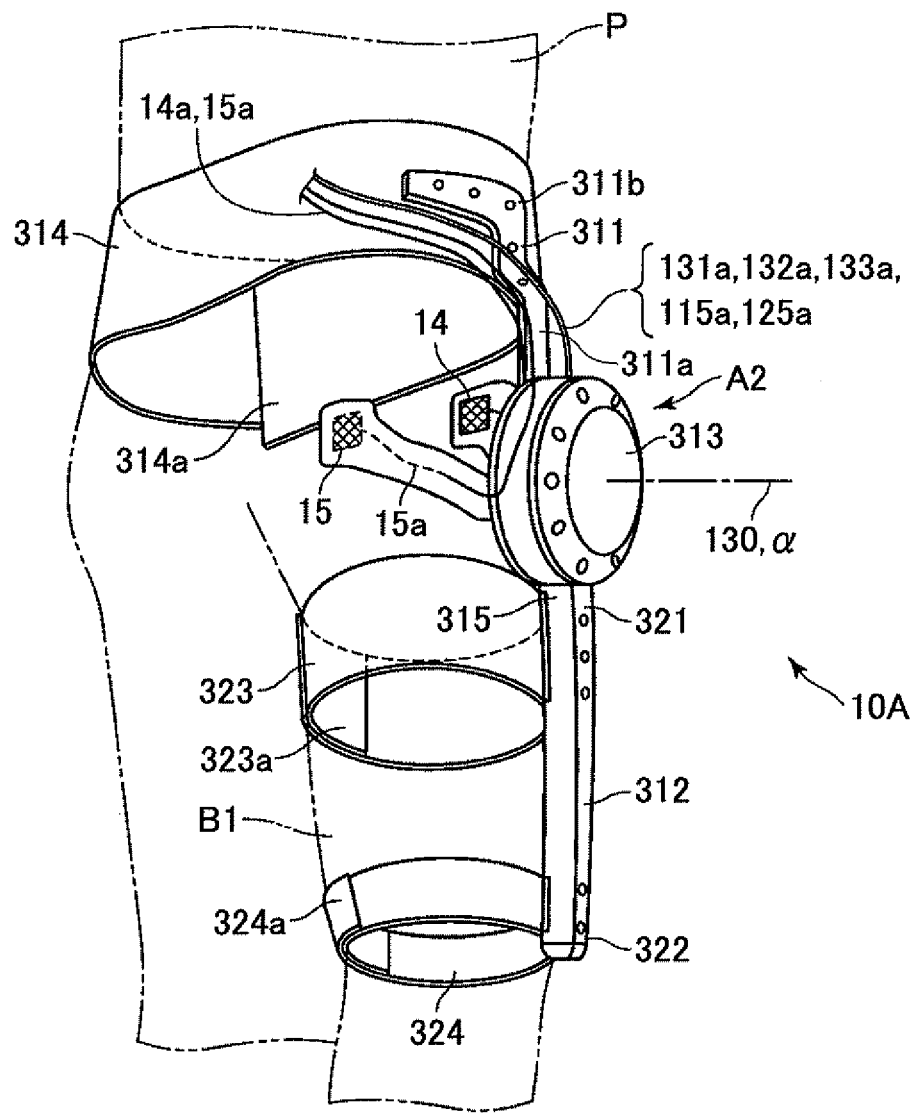
FIG. 11 is a perspective view illustrating a biometric measuring device for a hip joint used in a rehabilitation supporting device of a second embodiment of the invention.
Figure 12:
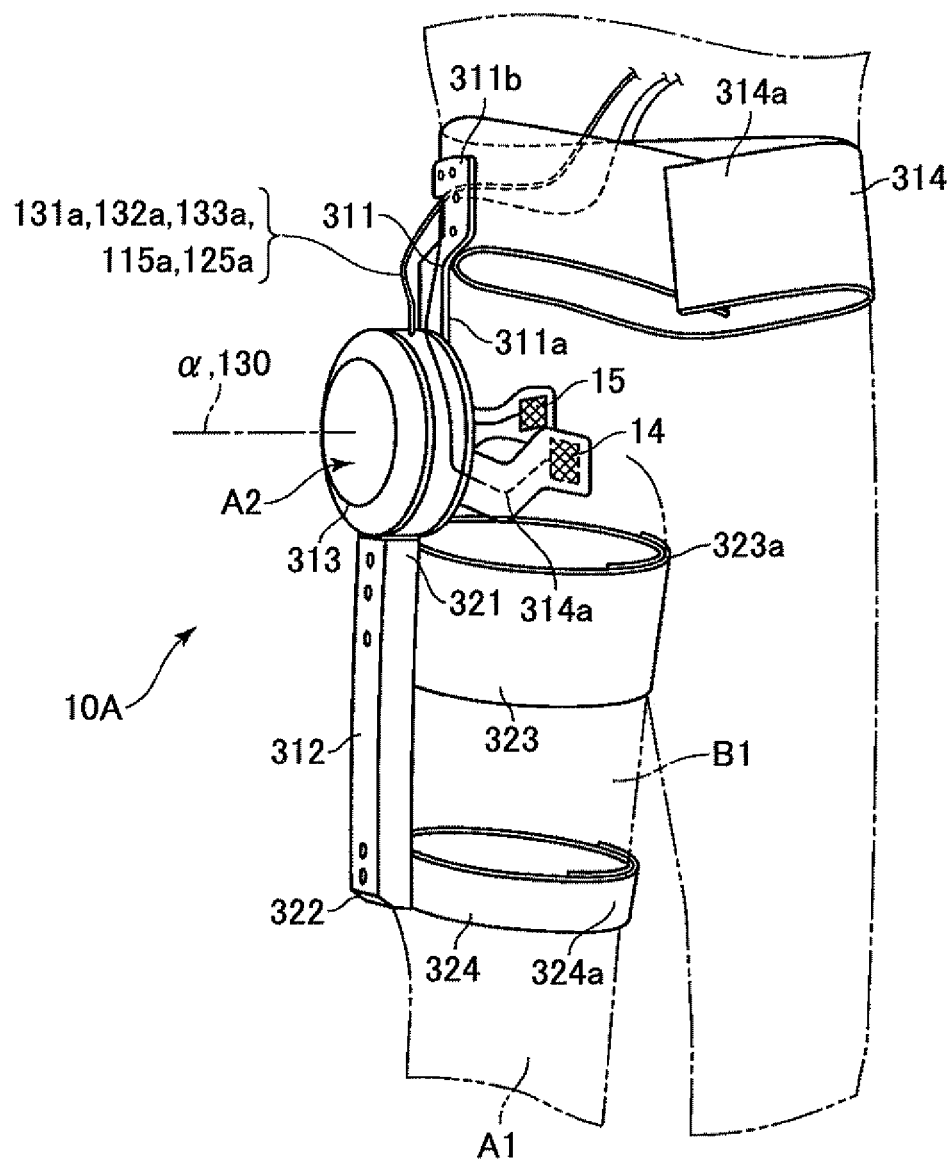
FIG. 12 is a perspective view of the biometric measuring device illustrated in FIG. 11 when viewed from the opposite side.

The biometric measuring device 10 of this embodiment includes a first frame 311, a second frame 312, a joint unit 313, the flexion-side biosignal sensor 14, and the extension-side biosignal sensor 15 as illustrated in FIGS. 11 and 12.

The lower end 311a of the first frame 311 is connected to the fixed side of the joint unit 313, and the upper end 311b of the first frame 311 extends toward the iliac crest of the pelvis (the first skeletal portion) extending from the hip joint A2, and turns around the back. The band 314 is attached to the upper end 311b of the first frame 311 which is located on the side away from the hip joint A2, and the band 314 is wound around the waist of the person P. An auxiliary belt may be disposed between croutche in order to avoid slipping up of the band 314 wound around the waist.

The second frame 312 is arranged along with the femur (the second skeletal portion), the upper end 321 of the second frame 312 is connected with the band 323 and the rotation side of the joint unit 313, and the lower end 322 of the second frame 312 is connected with the band 324. The bands 314, 323 and 324 have the composition that is the same as that of the bands 114, 123 and 124 of the first embodiment mentioned above.

As illustrated in FIGS. 11 and 12, the joint unit 313 connects the first frame 311 and the second frame 312, and the joint unit 313 is arranged coaxially with the rotation axis α around which flexion or extension is performed at the hip joint A2. The joint unit 313 includes an angle sensor 131, a drive unit 132, and a torque sensor 133, similar to the joint unit 13 of the first embodiment.

As illustrated in FIG. 12, the flexion-side biosignal sensor 14 is attached to the body surface corresponding to the iliopsoas or the tensor fasciae latae which mainly works as a voluntary muscle when flexion is performed at the hip joint A2. As illustrated in FIG. 11, the extension-side biosignal sensor 15 is attached to the body surface corresponding to the gluteus maximus which mainly works as a voluntary muscle when extension is performed at the hip joint A2. Because the outer skin at the locations where the flexion-side biosignal sensor 14 and the extension-side biosignal sensor 15 are disposed greatly expands or contracts during the operation, the signal lines 14a and 15a of the sensors have a suitable clearance to allow the movement.

The biometric measuring device 10A of this embodiment may be arranged so that the frame disposed along the upper thigh B1 is integral with the biometric measuring device 10 for the knee-joint A1 as illustrated in FIG. 1. In this case, a length adjusting device must be provided additionally because the length of the femur varies for every person P.

Figure 13:
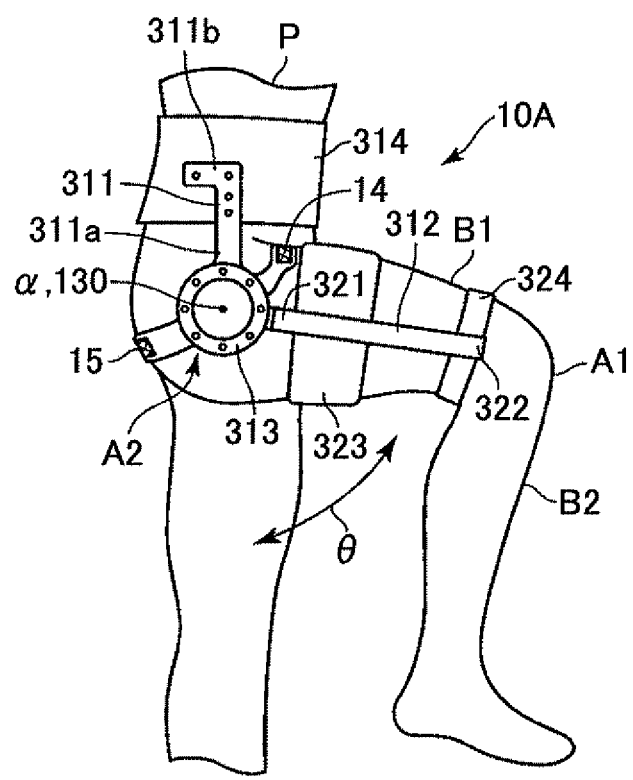
FIG. 13 is a side view illustrating the state of measuring a dynamic biosignal using the biometric measuring device illustrated in FIG. 11.

When the physical quantities around the hip joint A2 and the biosignals of the voluntary muscles, such as the iliopsoas, the tensor fasciae latae, and the gluteus maximus are measured, the person P is in a standing posture as illustrated in FIG. 13 and performs an operation which lifts and lowers the upper thigh B1. When it is difficult for the person P to stand straight, the person P may take either a seated posture or a lying-down posture as in FIGS. 1, 6 and 7. However, because the conditions of the gravity applied to the leg differ depending on the posture, it is necessary to take into consideration the state of condition. In such a case, the correlation between the physical quantities and the biosignals for every posture may be stored in the memory unit 34.

Next, a biometric measuring device 10B of a rehabilitation supporting device 1 of a third embodiment of the invention will be described with reference to FIGS. 14 and 15.

This biometric measuring device 10B is arranged for a stretching operation and a bending operation of an elbow joint A3. As illustrated in FIGS. 14 and 15, the biometric measuring device 10B includes a first frame 411, a second frame 412, a joint unit 413, the flexion-side biosignal sensor 14, and the extension-side biosignal sensor 15.

The first frame 411 is arranged along the humerus (the first skeletal portion) and fixed to the upper arm part B3 with the bands 413 and 414 which are disposed at two locations on the side close to the elbow joint A3 and on the side far from the elbow joint A3. The 2nd frame 12 is arranged along the ulna or the radius (the 2nd skeletal portion) and fixed to the forearm part B4 with the bands 423 and 424 which are disposed at two locations on the side close to the elbow joint A3 and on the side far from the elbow joint A3.

The joint unit 413 connects the first frame 411 and the second frame 412 of the biometric measuring device 10B and includes the angle sensor 131, the drive unit 132, and the torque sensor 133 which are built in the joint unit 413, similar to the joint unit 13 of the biometric measuring device 10 of the first embodiment. The joint unit 413 is arranged so that the rotation center 130 is coaxial with the rotation axis α around which stretching or bending operation of the elbow joint A3 is performed. That is, the biometric measuring device 10 of this embodiment does not support the pronation and supination operation of the elbow joint A3.

Figure 14:
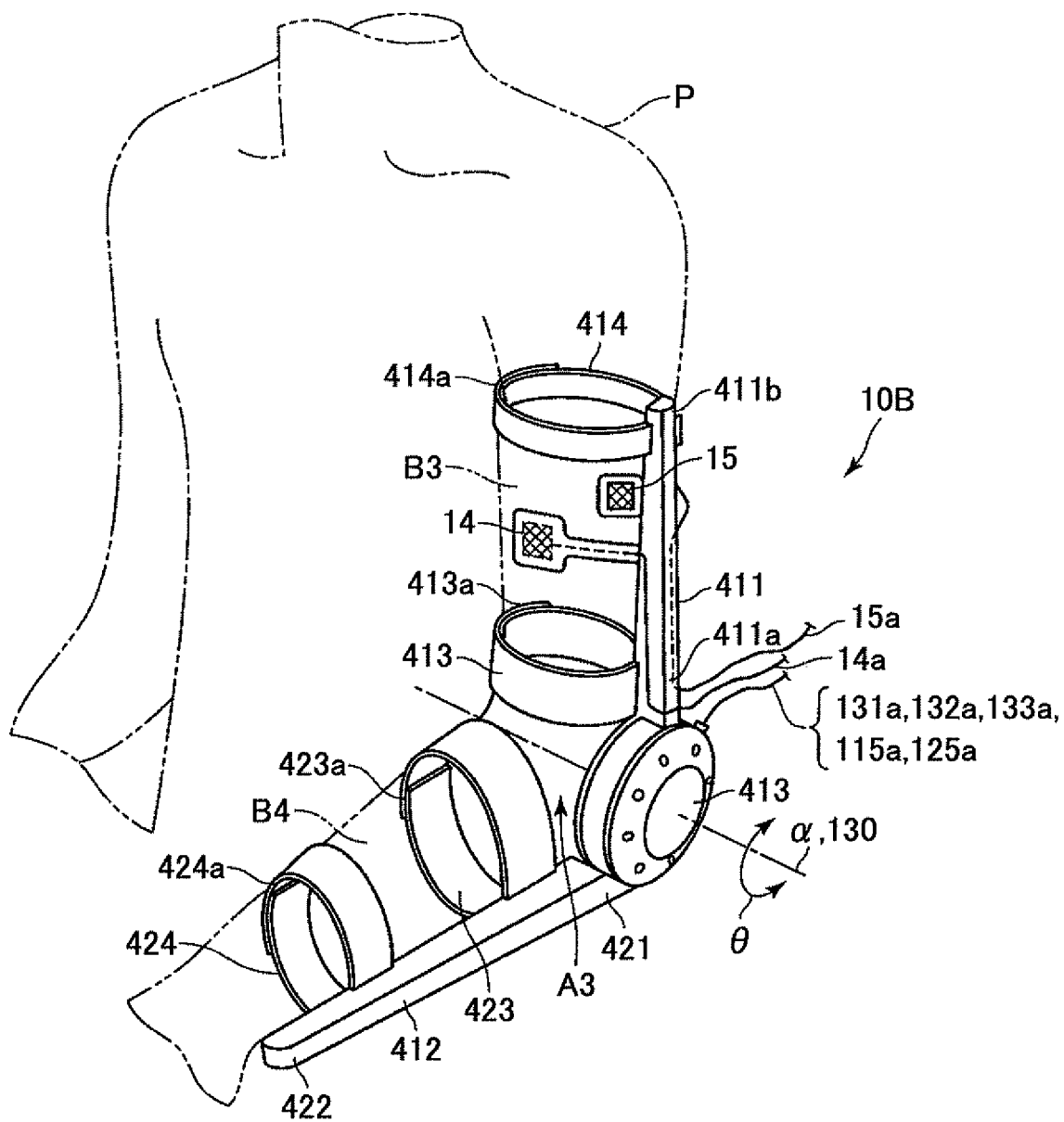
FIG. 14 is a perspective view illustrating a biometric measuring device for an elbow joint used in a rehabilitation supporting device of a third embodiment of the invention.

As illustrated in FIG. 14, the flexion-side biosignal sensor 14 is attached to the body surface corresponding to the biceps brachii and the brachialis which mainly work as a voluntary muscle when flexion is performed at the elbow joint A3. As illustrated in FIG. 15, the extension-side biosignal sensor 15 is attached to the body surface corresponding to the triceps brachii which mainly works as a voluntary muscle when extension is performed at the elbow joint A3. In the embodiment of FIGS. 14 and 15, the flexion-side biosignal sensor 14 and the extension-side biosignal sensor 15 are disposed at the locations that are distant from the bands 413 and 414. Because the flexion-side biosignal sensor 14 and the extension-side biosignal sensor 15 are to be attached to the positions where a biosignal is easily detected, they may be disposed on the inner circumferential surface of the band 413 on the side close to the elbow joint. A3.

Figure 15:
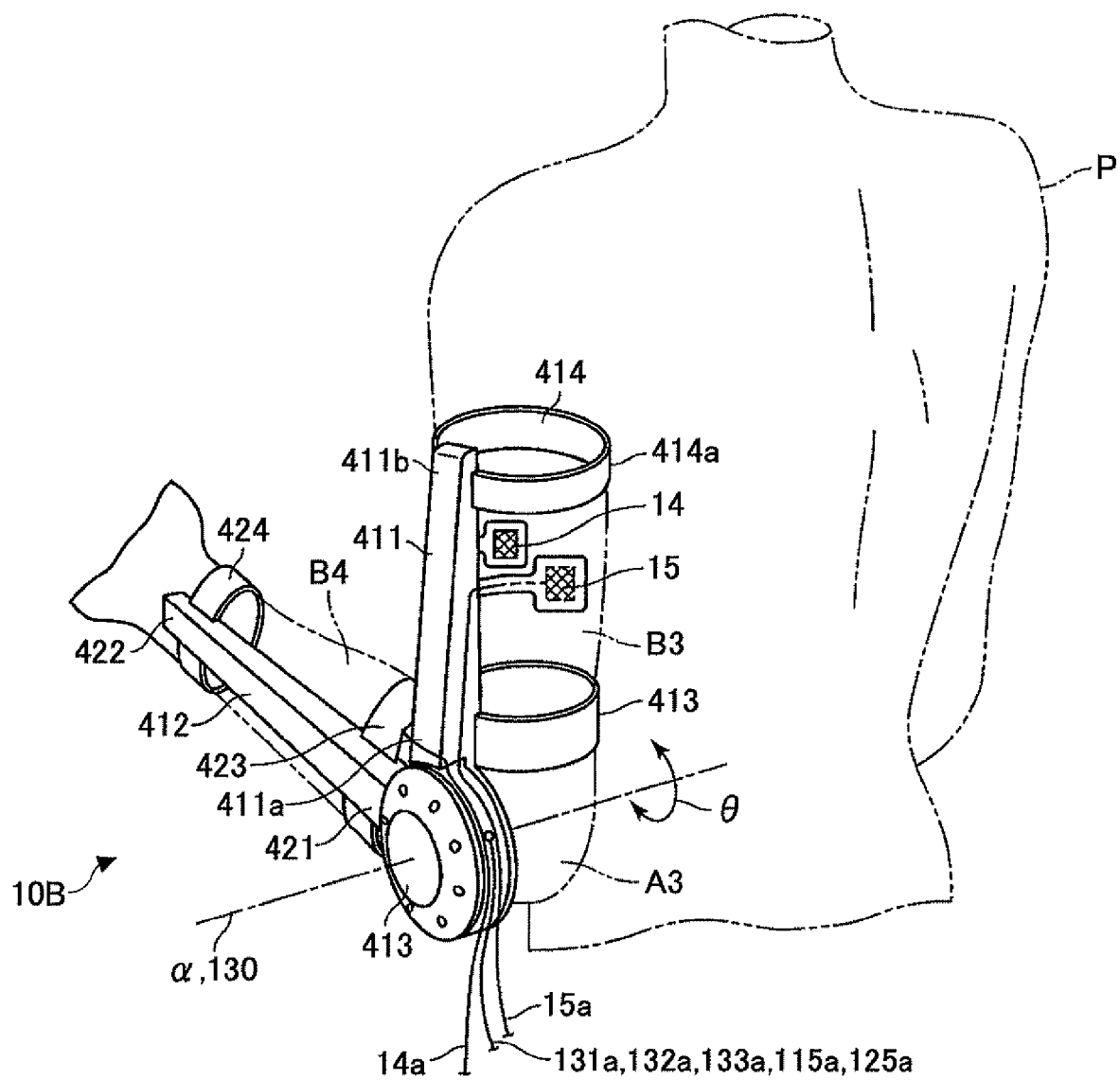
FIG. 15 is a perspective view of the biometric measuring device illustrated in FIG. 14 when viewed from the opposite side.

When the physical quantities around the elbow joint A3 and the biosignals of the voluntary muscles, such as the biceps brachii, the brachialis, and the triceps brachii are measured using the biometric measuring device 10B, the person P is in the posture in which the upper part of the body is raised, as illustrated in FIGS. 14 and 15, and bends or stretches the elbow. When it is difficult for the person P to be in the posture in which the upper part of the body is raised, the person P may take a seated posture or a lying-down posture. In this case, because the conditions of the gravity applied to the forearm part B4 differ depending on the posture, it is necessary to store the correlation between the physical quantities around the elbow joint A3 and the biosignals for every posture in the memory unit 34 similar to the second embodiment.

Next, a biometric measuring device 10C of a rehabilitation supporting device 1 of a fourth embodiment of the invention will be described with reference to FIG. 16.

This biometric measuring device 10G is arranged for bending (palmar flexion) and stretching (dorsiflex) of a wrist joint A4. The biometric measuring device 10 includes a first frame 511, a second frame 512, a joint unit 513, the flexion-side biosignal sensor 14, and the extension-side biosignal sensor 15.

Figure 16:
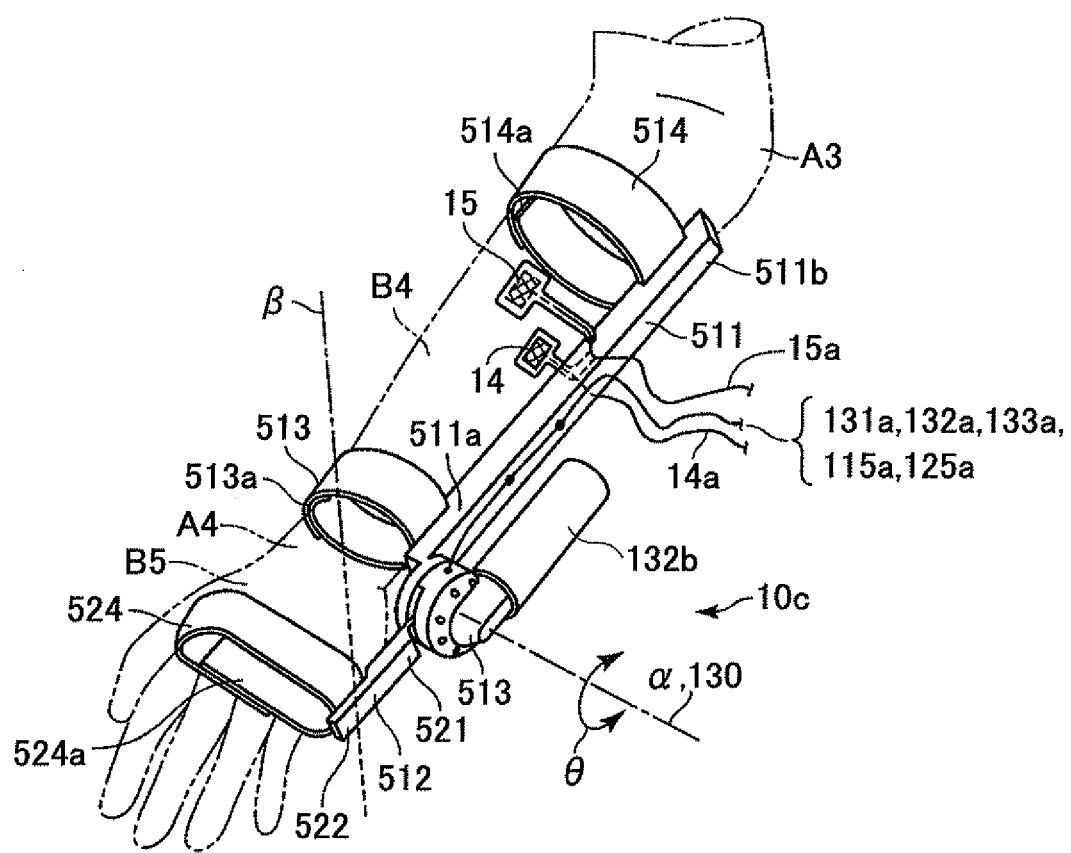
FIG. 16 is a perspective view illustrating a biometric measuring device for a wrist joint used in a rehabilitation supporting device of a fourth embodiment of the invention.

As illustrated in FIG. 16, the first frame 511 is arranged along the ulna (the first skeletal portion) and fixed to the forearm part B4 with the bands 513 and 514 which are disposed at two locations on the side near the wrist joint A4 and on the side near the elbow joint A3. The second frame 512 is arranged along the metatarsal (the second skeletal portion) on the ulna side, and fixed to the palm B5 with the band 524 which is attached to the second frame 512 on the side far from the wrist joint A4 and wound around the end side of the second to fifth metatarsals.

The joint unit 513 is arranged coaxially with a rotation axis α which is assumed to pass through the wrist joint A4 from the radius side to the ulna side as illustrated in FIG. 16. The joint unit 513 includes the angle sensor 131, the drive unit 132, and the torque sensor 133 which are built in the joint unit 513, similar to the previously described embodiments. Because the motor 132b is arranged along the first frame 511, the drive unit 132 differs in appearance, but the function of the drive unit 132 is the same as that of the drive unit of other embodiments.

The flexion-side biosignal sensor 14 is attached to the body surface corresponding to any of the flexor digitorum superficialis, the flexor digitorum profundus, the flexor carpi ulnaris, the flexor pollicis longus, the flexor carpi radialis, etc. which mainly work when flexion is performed at the wrist joint A4. The extension-side biosignal sensor 15 is attached to the body surface corresponding to any of the extensor digitorum, the extensor carpi radialis longus, the extensor carpi radialis brevis, etc. which mainly work when extension is performed at the wrist joint A4.

As is apparent from the structure of FIG. 16, this biometric measuring device 10C may be used also for measurement of the physical quantities of the flexion-side and extension-side displacements of the wrist joint A4 and the biosignals. When the physical quantities of the flexion-side and extension-side displacements and the biosignals are measured, the biometric measuring device 10C is attached so that the joint unit 513 is disposed on the back side of the hand. The rotation center 530 of the joint unit 513 is arranged coaxially with the axis β of the wrist joint which is assumed to pass through the capitate bone in the direction from the palm side to the back side.

The posture of the forearm part B4 when measuring a biosignal may be set in any direction. However, when the current measuring result is compared with the previous measuring result in the process of rehabilitation, the forearm part B4 is held in the same posture, or the correlation between the physical quantities of the wrist joint and the biosignals is stored for every posture.

As described in the foregoing, the biometric measuring device 10 including the frame adaptable for the joint of the living body and the skeletal portion extending from the joint may be arranged not only in accordance with the joint parts of the first to fourth embodiments but also in accordance with other joints. For example, the biometric measuring device 10 may be arranged in accordance with any of an ankle, a shoulder, and finger joints. When it is applied to finger joints, a plunger-type actuator in which the wire and the solenoid are combined, a fluid-pressure actuator, an ultrasonic motor, etc. may be used in order to minimize the size of the drive unit 132.

In the first embodiment, the display unit 40 and the simulation unit 20 are illustrated as the indicating unit which provides visual and tangible information. However, the indicating unit may be arranged to output the physical quantities of the joint and the biosignals of the voluntary muscle measured by the biometric measuring device 10 in a quantitative manner. For example, the indicating unit may be arranged to provide audio information which is recognized according to the frequency or amplitude of sound.

In the previously described embodiments, the biometric measuring devices 10, 10A-10C each of which is applied to one joint are illustrated. However, as illustrated in FIG. 1, the biometric measuring device 10 may be arranged to measure the hip joint A2 and the knee joint A1 simultaneously. Alternatively, the biometric measuring devices 10, 10A-10C may be arranged in combination suitably. Alternatively, the biometric measuring device 10 may be arranged to measure the right leg and the left leg simultaneously. Alternatively, the biometric measuring device 10 may be arranged to measure the upper limb and the lower limb simultaneously.

In the previously described embodiments, the first frames 11, 311, 411, 511 and the second frames 12, 312, 412, 512 are arranged along the body surface of the person P. It is adequate that the rotation center 130 of the joint unit 13 is arranged to be coaxial with the rotation axis α of the joint as the object of measurement. Therefore, the first frame 11 and the second frame 12 may be arranged along the first skeletal portion and the second skeletal portion to extend from the joint unit 13 to the bodily front or the bodily back in order to make the weight of the person P easily applied to the joint unit 13.

The flexion-side correction value and the extension-side correction value may be coefficients for determining the correlation between the biosignal when the flexor and the extensor are energized and the corresponding muscular force. The flexion-side correction value and the extension-side correction value may be represented by a fixed value or a polynomial.

This international application is based upon and claims the benefit of priority of Japanese patent application No. 2007-075632, filed on Mar. 22, 2007, and Japanese patent application No. 2008-056674, filed on Mar. 6, 2008, the contents of which is hereby incorporated by reference in their entirety.

Industrial Applicability

Although the rehabilitation supporting device of the embodiment has been applied to the joint of the human body, it is applicable also to a joint of an animal having an internal skeleton as a living body.

The invention claimed is:

1. A rehabilitation supporting device comprising:
a first frame arranged along a first skeletal portion extending from a joint as an object of measurement among moving parts of a living body;
a second frame arranged along a second skeletal portion extending from the joint in a direction different from a direction of the first skeletal portion;
an angle sensor, a center of rotation of which is arranged to be coaxial with a rotation axis of the joint, the angle sensor detecting a rotational angle position between the first frame and the second frame;
a flexion-side biosignal sensor arranged to contact a body surface corresponding to a flexor which bends the joint connecting the first skeletal portion and the second skeletal portion, the flexion-side biosignal sensor detecting a biosignal of the flexor;

an extension-side biosignal sensor arranged to contact a body surface corresponding to an extensor which stretches the joint connecting the first skeletal portion and the second skeletal portion, the extension-side biosignal sensor detecting a biosignal of the extensor;

a calibration unit arranged to determine a flexion-side correction value to correct an output value of the flexion-side biosignal sensor and an extension-side correction value to calibrate an output value of the extension-side biosignal sensor individually;

a memory unit arranged to store individual correction values of the biosignals for individuals, the flexion-side correction value, and the extension-side correction value, a first strain gage which is attached to the first frame and measures a first bending stress applied to the first frame; and a second strain gage which is attached to the second frame and which measures a second bending stress applied to the second frame, wherein the calibration unit is configured to obtain the first and second bending stresses from the first and second strain gages to determine the flexion-side correction value and the extension-side correction value, wherein the rehabilitation supporting device further comprises:

an indicating unit arranged to provide visual, audio or tangible information which is recognized by at least one of vision, hearing and tactile senses, said indicating unit being arranged to output the information based on a flexor output signal obtained from an output value of the flexion-side biosignal sensor which is corrected based on the flexion-side correction value, an extensor output signal obtained from an output value of the extension-side biosignal sensor which is corrected based on the extension-side correction value, and the rotational angle position detected by the angle sensor, and wherein the indicating unit includes a simulation unit arranged to provide visual or tangible information, the simulation unit comprising:

a first simulation frame and a second simulation frame arranged independently of the first frame and the second frame, an end of the first simulation frame being rotatably connected to an end of the second simulation frame by a connection part;

a simulation object angle sensor arranged in the connection part to detect a rotational angle position of the first simulation frame and the second simulation frame;

a simulation object drive unit arranged coaxially with a center of rotation of the simulation object angle sensor, the simulation object drive unit rotating the second simulation frame to the first simulation frame; and a simulation object control part arranged to cause the simulation object drive unit to rotate the first simulation frame and the second simulation frame by converting the flexor output signal obtained from the output value of the flexion-side biosignal sensor corrected based on the flexion-side correction value, the extensor output signal obtained from the output value of the extension-side biosignal sensor corrected based on the extension-side correction value, and the rotational angle position of the angle sensor into output signals to the simulation object drive unit.

2. The rehabilitation supporting device according to claim 1, wherein the flexion-side biosignal sensor measures, as the biosignal of the flexor, at least one of a flexion-side neurotransmission signal corresponding to the flexor, sent from a brain to contract the flexor, and a flexion-side myoelectric potential signal arising when the flexor is contracted, and the extension-side biosignal sensor measures, as the biosignal of the extensor, at least one of an extension-side neurotransmission signal corresponding to the extensor, output from the brain to contract the extensor, and an extension-side myoelectric potential signal arising when the extensor is contracted.

3. The rehabilitation supporting device according to claim 1, wherein the calibration unit is arranged to determine the flexion-side correction value and the extension-side correction value based on an amount of change of a rotational angle detected by the angle sensor, a time for the first frame to be rotated relative to the second frame to reach the amount of change of the rotational angle, and an impulse determined from an output value of the flexion-side biosignal sensor and an output value of the extension-side biosignal sensor while the first frame is rotated relative to the second frame until the amount of change of the rotational angle is reached.

4. The rehabilitation supporting device according to claim 1, further comprising:

a drive unit arranged coaxially with a center, of rotation of the angle sensor, the drive unit rotating the first frame toward the second frame;

a torque sensor arranged coaxially with the center of rotation of the angle sensor, the torque sensor detecting a torque which rotates the first frame toward the second frame; and a control unit arranged to operate the drive unit based on information acquired from the flexion-side biosignal sensor, the extension-side biosignal sensor, the angle sensor and the torque sensor, and the respective correction values acquired from the calibration unit.

5. The rehabilitation supporting device according to claim 4, wherein, when the joint is not in action, the control unit causes the drive unit to apply a load of a predetermined torque to the joint, and wherein the calibration unit is arranged to determine, when the flexor and the extensor respectively act to withstand the load of the predetermined torque in order to maintain a posture of the joint, the flexion-side correction value and the extension-side correction value based on respective output values of the flexion-side biosignal sensor, the extension-side biosignal sensor, and the torque sensor.

6. The rehabilitation supporting device according to claim 4, further comprising a correction unit arranged to output, to the control unit, a flexor output signal obtained from an output value of the flexion-side biosignal sensor corrected based on the flexion-side correction value, and an extensor output signal obtained an output value of the extension-side biosignal sensor corrected based on the extension-side correction value, wherein the control unit operates the drive unit based on the flexor output signal and the extensor output signal from the correction unit, and the rotational angle position from the angle sensor.

7. The rehabilitation supporting device according to claim 1, further comprising:

a fixture arranged to fix a relative angle between the first frame and the second frame at an arbitrary rotational angle.

8. The rehabilitation supporting device according to claim 7, wherein the calibration unit determines, when the first frame is fixed to the second frame at the arbitrary rotational angle by the fixture and the flexor and the extensor act to rotate the first frame to the second frame, the flexion-side correction value and the extension-side correction value based on information acquired from the flexion-side biosignal sensor, the extension-side biosignal sensor, the first strain gage, and the second strain gage.

9. The rehabilitation supporting device according to claim 1, wherein the indicating unit includes a display unit arranged to display the flexor output signal, the extensor output signal, and the rotational angle position.

10. The rehabilitation supporting device according to claim 1, further comprising:
   a drive unit arranged coaxially with a center of rotation of the angle sensor, the drive unit rotating the first frame toward the second frame;
   a torque sensor arranged coaxially with the center of rotation of the angle sensor, the torque sensor detecting a torque which rotates the first frame toward the second frame; and
   a control unit arranged to operate the drive unit based on the flexor output signal, the extensor output signal, the rotational angle position of the angle sensor, a detection value of the torque sensor, a detection value of the first strain gage, and a detection value of the second strain gage.

11. The rehabilitation supporting device according to claim 10, wherein the control unit is arranged to operate the drive unit based on a rotational angle position of the simulation object angle sensor, and
   wherein the simulation object control part is arranged to operate the simulation object drive unit based on the flexor output signal, the extensor output signal, the rotational angle position of the angle sensor, the detection value of the torque sensor, the detection value of the first strain gage, and the detection value of the second strain gage.

* * * * *